US008992516B2

(12) United States Patent
Muller

(10) Patent No.: US 8,992,516 B2
(45) Date of Patent: Mar. 31, 2015

(54) EYE THERAPY SYSTEM

(75) Inventor: David Muller, Boston, MA (US)

(73) Assignee: Avedro, Inc., Waltham, MA (US)

(*) Notice: Subject to any disclaimer, the term of this patent is extended or adjusted under 35 U.S.C. 154(b) by 547 days.

(21) Appl. No.: 11/898,189

(22) Filed: Sep. 10, 2007

(65) Prior Publication Data
US 2009/0024117 A1    Jan. 22, 2009

Related U.S. Application Data

(60) Provisional application No. 60/929,946, filed on Jul. 19, 2007.

(51) Int. Cl.
| A61B 18/18 | (2006.01) |
| A61B 18/14 | (2006.01) |
| A61F 9/007 | (2006.01) |
| A61B 18/00 | (2006.01) |
| A61B 18/22 | (2006.01) |
| A61F 9/009 | (2006.01) |

(Continued)

(52) U.S. Cl.
CPC ....... *A61B 18/14* (2013.01); *A61B 2018/00023* (2013.01); *A61B 18/1477* (2013.01); *A61B 18/18* (2013.01); *A61B 18/22* (2013.01); *A61B 2018/00005* (2013.01); *A61B 2018/00029* (2013.01); *A61B 2018/00702* (2013.01); *A61B 2018/00791* (2013.01); *A61B 2018/1425* (2013.01); *A61B 2018/1807* (2013.01); *A61F 9/0079* (2013.01); *A61F 9/009* (2013.01); *A61F 2009/00853* (2013.01); *A61F 2009/00872* (2013.01); *A61N 1/36046* (2013.01); *A61N 1/403* (2013.01)
USPC .................................. 606/41; 606/20; 606/27

(58) Field of Classification Search
CPC ................................ A61B 18/14; A61B 18/18
See application file for complete search history.

(56) References Cited

U.S. PATENT DOCUMENTS

| 3,073,310 A | 1/1963 | Mocarski |
| 3,776,230 A | 12/1973 | Neefe |

(Continued)

FOREIGN PATENT DOCUMENTS

| EP | 1 561 440 | 8/2005 |
| EP | 2 269 531 | 1/2011 |

(Continued)

OTHER PUBLICATIONS

International Search Report for PCT/US08/76023, dated Nov. 25, 2008, 4 pages.

(Continued)

*Primary Examiner* — Lynsey Crandall
(74) *Attorney, Agent, or Firm* — McDonnell Boehnen Hulbert & Berghoff LLP

(57) ABSTRACT

A system for applying therapy to an eye selectively applies coolant to the corneal surface to minimize heat-related damage to the corneal surface during thermokeratoplasty. Embodiments may include an energy source, a conducting element, a coolant supply, and at least one coolant delivery element. The conducting element is operably connected to the energy source and extends from a proximal end to a distal end. The conducting element directs energy from the energy source to the distal end, which is positionable at the eye. The coolant delivery elements are in communication with the coolant supply and are operable to deliver a micro-controlled pulse of coolant to the distal end.

39 Claims, 7 Drawing Sheets

(51) Int. Cl.
*A61F 9/008* (2006.01)
*A61N 1/36* (2006.01)
*A61N 1/40* (2006.01)

(56) References Cited

U.S. PATENT DOCUMENTS

| | | | |
|---|---|---|---|
| 4,043,342 A | 8/1977 | Morrison, Jr. | |
| 4,326,529 A | 4/1982 | Doss et al. | |
| 4,381,007 A * | 4/1983 | Doss | 606/27 |
| 4,429,960 A | 2/1984 | Mocilac et al. | |
| 4,481,948 A | 11/1984 | Sole | |
| 4,490,022 A | 12/1984 | Reynolds | |
| 4,546,773 A | 10/1985 | Kremer et al. | |
| 4,712,543 A | 12/1987 | Baron | |
| 4,743,725 A | 5/1988 | Risman | |
| 4,796,623 A | 1/1989 | Krasner et al. | |
| 4,805,616 A | 2/1989 | Pao | |
| 4,881,543 A | 11/1989 | Trembly et al. | |
| 4,891,043 A | 1/1990 | Zeimer et al. | |
| 4,943,296 A | 7/1990 | Funakubo et al. | |
| 4,994,058 A | 2/1991 | Raven et al. | |
| 5,019,074 A | 5/1991 | Muller | |
| 5,080,660 A | 1/1992 | Buelna | |
| 5,103,005 A | 4/1992 | Gyure et al. | |
| 5,123,422 A | 6/1992 | Charvin | |
| 5,171,254 A | 12/1992 | Sher | |
| 5,281,211 A | 1/1994 | Parel et al. | |
| 5,332,802 A | 7/1994 | Kelman et al. | |
| 5,368,604 A | 11/1994 | Kilmer et al. | |
| 5,370,644 A | 12/1994 | Langberg | |
| 5,395,385 A | 3/1995 | Kilmer et al. | |
| 5,437,658 A | 8/1995 | Muller et al. | |
| 5,461,212 A | 10/1995 | Seiler et al. | |
| 5,490,849 A | 2/1996 | Smith | |
| 5,586,134 A | 12/1996 | Das et al. | |
| 5,591,185 A | 1/1997 | Kilmer et al. | |
| 5,618,284 A | 4/1997 | Sand | |
| 5,624,456 A | 4/1997 | Hellenkamp | |
| 5,626,595 A | 5/1997 | Sklar et al. | |
| 5,634,921 A | 6/1997 | Hood et al. | |
| 5,658,278 A | 8/1997 | Imran et al. | |
| 5,695,448 A | 12/1997 | Kimura et al. | |
| 5,766,171 A | 6/1998 | Silvestrini | |
| 5,779,696 A | 7/1998 | Berry et al. | |
| 5,814,040 A | 9/1998 | Nelson et al. | |
| 5,830,139 A | 11/1998 | Abreu | |
| 5,873,901 A | 2/1999 | Wu et al. | |
| 5,885,275 A | 3/1999 | Muller | |
| 5,910,110 A | 6/1999 | Bastable | |
| 5,919,222 A | 7/1999 | Hjelle et al. | |
| 5,938,674 A | 8/1999 | Terry | |
| 5,941,834 A | 8/1999 | Skladnev et al. | |
| 6,033,396 A | 3/2000 | Huang et al. | |
| 6,036,688 A | 3/2000 | Edwards | |
| 6,053,909 A | 4/2000 | Shadduck | |
| 6,101,411 A | 8/2000 | Newsome | |
| 6,104,959 A * | 8/2000 | Spertell | 607/101 |
| 6,110,182 A | 8/2000 | Mowlai-Ashtiani | |
| 6,120,434 A | 9/2000 | Kimura et al. | |
| 6,139,876 A | 10/2000 | Kolta | |
| 6,149,646 A | 11/2000 | West, Jr. et al. | |
| 6,161,544 A | 12/2000 | DeVore et al. | |
| 6,162,210 A | 12/2000 | Shadduck | |
| 6,213,997 B1 | 4/2001 | Hood et al. | |
| 6,293,938 B1 | 9/2001 | Muller | |
| 6,319,273 B1 | 11/2001 | Chen et al. | |
| 6,325,792 B1 | 12/2001 | Swinger et al. | |
| 6,334,074 B1 | 12/2001 | Spertell | |
| 6,342,053 B1 | 1/2002 | Berry | |
| 6,402,739 B1 | 6/2002 | Neev | |
| 6,413,255 B1 | 7/2002 | Stern | |
| 6,520,956 B1 | 2/2003 | Huang | |
| 6,617,963 B1 | 9/2003 | Watters et al. | |
| 6,749,604 B1 | 6/2004 | Eggers et al. | |
| 6,918,906 B2 | 7/2005 | Long | |
| 6,946,440 B1 | 9/2005 | DeWoolfson et al. | |
| 7,044,945 B2 | 5/2006 | Sand | |
| 7,130,835 B2 | 10/2006 | Cox et al. | |
| 7,141,049 B2 | 11/2006 | Stern et al. | |
| 7,192,429 B2 | 3/2007 | Trembly | |
| 7,270,658 B2 | 9/2007 | Woloszko et al. | |
| 7,402,562 B2 | 7/2008 | DeWoolfson | |
| 7,651,506 B2 | 1/2010 | Bova et al. | |
| 7,713,268 B2 | 5/2010 | Trembly | |
| 7,875,024 B2 | 1/2011 | Turovskiy et al. | |
| 7,976,542 B1 | 7/2011 | Cosman et al. | |
| 8,177,778 B2 | 5/2012 | Muller et al. | |
| 8,348,935 B2 | 1/2013 | Muller et al. | |
| 8,398,628 B2 | 3/2013 | Muller | |
| 8,409,189 B2 | 4/2013 | Muller | |
| 2001/0021844 A1 | 9/2001 | Kurtz et al. | |
| 2001/0034502 A1 | 10/2001 | Moberg et al. | |
| 2001/0039422 A1 | 11/2001 | Carol et al. | |
| 2002/0002369 A1 | 1/2002 | Hood | |
| 2002/0013579 A1 | 1/2002 | Silvestrini | |
| 2002/0022873 A1 | 2/2002 | Erickson et al. | |
| 2002/0035345 A1 | 3/2002 | Beck | |
| 2002/0049437 A1 | 4/2002 | Silvestrini | |
| 2002/0077699 A1 | 6/2002 | Olivieri et al. | |
| 2002/0091323 A1 | 7/2002 | Dreher | |
| 2002/0091401 A1 | 7/2002 | Hellenkamp | |
| 2002/0099363 A1 | 7/2002 | Woodward et al. | |
| 2002/0143326 A1 | 10/2002 | Foley et al. | |
| 2002/0164379 A1 | 11/2002 | Nishihara et al. | |
| 2003/0018255 A1 | 1/2003 | Martin et al. | |
| 2003/0097130 A1 | 5/2003 | Muller et al. | |
| 2003/0167061 A1 | 9/2003 | Schlegel et al. | |
| 2003/0175259 A1 | 9/2003 | Karageozian | |
| 2003/0181903 A1 | 9/2003 | Hood et al. | |
| 2003/0216728 A1 * | 11/2003 | Stern et al. | 606/41 |
| 2004/0001821 A1 | 1/2004 | Silver et al. | |
| 2004/0002640 A1 | 1/2004 | Luce | |
| 2004/0049186 A1 | 3/2004 | Hood et al. | |
| 2004/0111086 A1 | 6/2004 | Trembly | |
| 2004/0143250 A1 * | 7/2004 | Trembly | 606/33 |
| 2004/0199158 A1 | 10/2004 | Hood et al. | |
| 2004/0243160 A1 | 12/2004 | Shiuey et al. | |
| 2005/0033202 A1 | 2/2005 | Chow et al. | |
| 2005/0070977 A1 | 3/2005 | Molina | |
| 2005/0131401 A1 | 6/2005 | Malecki et al. | |
| 2005/0183732 A1 | 8/2005 | Edwards | |
| 2005/0197657 A1 | 9/2005 | Goth et al. | |
| 2005/0241653 A1 | 11/2005 | Van Heugten et al. | |
| 2005/0267332 A1 | 12/2005 | Paul et al. | |
| 2005/0287217 A1 | 12/2005 | Levin et al. | |
| 2006/0135957 A1 | 6/2006 | Panescu | |
| 2006/0149343 A1 * | 7/2006 | Altshuler et al. | 607/90 |
| 2006/0189964 A1 * | 8/2006 | Anderson et al. | 606/9 |
| 2006/0206110 A1 | 9/2006 | Knowlton et al. | |
| 2006/0254851 A1 | 11/2006 | Karamuk | |
| 2006/0287649 A1 | 12/2006 | Ormsby et al. | |
| 2006/0287662 A1 | 12/2006 | Berry et al. | |
| 2007/0048340 A1 | 3/2007 | Ferren et al. | |
| 2007/0055227 A1 | 3/2007 | Khalaj et al. | |
| 2007/0074722 A1 | 4/2007 | Giroux et al. | |
| 2007/0074730 A1 | 4/2007 | Nanduri et al. | |
| 2007/0114946 A1 | 5/2007 | Goetze et al. | |
| 2007/0123845 A1 | 5/2007 | Lubatschowski | |
| 2007/0161976 A1 | 7/2007 | Trembly | |
| 2007/0179564 A1 | 8/2007 | Harold | |
| 2007/0191909 A1 | 8/2007 | Ameri et al. | |
| 2007/0203547 A1 * | 8/2007 | Costello et al. | 607/59 |
| 2007/0244470 A1 | 10/2007 | Barker et al. | |
| 2007/0244496 A1 | 10/2007 | Hellenkamp | |
| 2008/0015660 A1 | 1/2008 | Herekar | |
| 2008/0027328 A1 | 1/2008 | Klopotek et al. | |
| 2008/0300590 A1 | 12/2008 | Horne et al. | |
| 2009/0024117 A1 | 1/2009 | Muller | |
| 2009/0054879 A1 | 2/2009 | Berry | |
| 2009/0069798 A1 | 3/2009 | Muller et al. | |
| 2009/0149842 A1 | 6/2009 | Muller et al. | |
| 2009/0149923 A1 | 6/2009 | Herekar | |
| 2009/0171305 A1 | 7/2009 | El Hage | |
| 2009/0187173 A1 | 7/2009 | Muller | |

(56) References Cited

U.S. PATENT DOCUMENTS

| | | | |
|---|---|---|---|
| 2009/0187178 | A1 | 7/2009 | Muller et al. |
| 2009/0209954 | A1 | 8/2009 | Muller et al. |
| 2009/0275936 | A1 | 11/2009 | Muller |
| 2010/0094197 | A1 | 4/2010 | Marshall et al. |
| 2010/0094280 | A1 | 4/2010 | Muller |
| 2010/0185192 | A1 | 7/2010 | Muller et al. |
| 2010/0256626 | A1 | 10/2010 | Muller et al. |
| 2010/0256705 | A1 | 10/2010 | Muller et al. |
| 2010/0280509 | A1 | 11/2010 | Muller et al. |

FOREIGN PATENT DOCUMENTS

| | | |
|---|---|---|
| WO | WO 99/17690 | 4/1999 |
| WO | WO 00/09027 | 2/2000 |
| WO | WO 00/74648 | 12/2000 |
| WO | WO 03/002008 | 1/2003 |
| WO | WO 2004/052223 | 6/2004 |
| WO | 2006128038 A2 | 11/2006 |
| WO | WO 2006/128038 A2 | 11/2006 |
| WO | WO 2007/022993 | 3/2007 |
| WO | 2007/120457 A2 | 10/2007 |
| WO | WO 2008/008330 | 1/2008 |
| WO | WO 2009/012490 | 1/2009 |
| WO | WO 2009/073213 | 6/2009 |
| WO | WO 2009/094467 | 7/2009 |
| WO | WO 2010/039854 | 4/2010 |
| WO | WO 2011/050164 | 4/2011 |

OTHER PUBLICATIONS

Written Opinion for PCT/US08/76023, dated Nov. 25, 2008, 7 pages.
International Search Report for PCT/US08/70640, dated Dec. 22, 2008, 7 pages.
Written Opinion for PCT/US08/70640, dated Dec. 22, 2008, 12 pages.
Muller et al., Br. J. Opthalmol 2001; 85:437-443 (April).
Naoumidi et al., J. Cataract Refract Surg. May 2006; 32(5):732-41.
Pallikaris et al., J. Cataract Refract Surg. Aug. 2005; 31(8):1520-29.
Acosta et al., Cornea. Aug. 2006;25(7):830-8.
Alain Chandonnet et al., "$CO_2$ Laser Annular Thermokeratoplasty: A Preliminary Study", Lasers in Surgery and Medicine 12:264-273 (1992), Wiley-Lill, Inc., pp. 264-273.
Berjano et al.; "Radio-Frequency Heating of the Cornea: Theoretical Model and In Vitro Experiments"; IEEE Transactions on Biomedical Engineering; vol. 49; No. 3; Mar. 2002; pp. 196-205.
Berjano et. al.; "Ring Electrode for Radio-Frequency Heating of the Cornea: Modelling and In Vitro Experiments"; Medical & Biological Engineering & Computing 2003; vol. 41; pp. 630-639.
International Search Report mailed Aug. 14, 2009 for PCT/US2009/042204, (5 pages).
International Search Report mailed Nov. 20, 2009 for PCT/2009/059061 (3 pages).
International Search Report mailed Nov. 6, 2009 for PCT/US2009/057481 (2 pages).
Alió JL, Amparo F, Ortiz D, Moreno L, "Corneal Multifocality With Excimer Laser for Presbyopia Correction," *Current Opinion in Ophthalmology*, vol. 20, Jul. 2009, pp. 264-271 (8 pages).
Alió JL, Chaubard JJ, Caliz A, Sala E, Patel S, "Correction of Presbyopia by Technovision Central Multifocal LASIK (PresbyLASIK)," *Journal of Refractive Surgery*, vol. 22, May 2006, pp. 453-460 (8 pages).
Anderson K, El-Sheikh A, Newson T, "Application of Structural Analysis to the Mechanical Behavior of the Cornea," *Journal of the Royal Society Interface*, vol. 1, May 2004, pp. 3-15 (13 pages).
Andreassen TT, Simonsen AH, Oxlund H, "Biomechanical Properties of Keratoconus and Normal Corneas," *Experimental Eye Research*, vol. 31, Oct. 1980, pp. 435-441 (7 pages).
Anschutz T, "Laser Correction of Hyperopia and Presbyopia," *International Ophthalmology Clinics*, vol. 34, No. 4, Fall 1994, pp. 107-137 (33 pages).

Bailey MD, Zadnik K, "Outcomes of LASIK for Myopia With FDA-Approved Lasers," *Cornea*, vol. 26, No. 3, Apr. 2007, pp. 246-254 (9 pages).
Borja D, Manns F, Lamar P, Rosen A, Fernandez V, Parel JM, "Preparation and Hydration Control of Corneal Tissue Strips for Experimental Use," *Cornea*, vol. 23, No. 1, Jan. 2004, pp. 61-66 (7 pages).
Bower KS, Weichel ED, Kim TJ, "Overview of Refractive Surgery," *Am Fam Physician*, vol. 64, No. 7, Oct. 2001, pp. 1183-1190 (8 pages).
Braun EH, Lee J, Steinert RF, "Monovision in LASIK," *Ophthalmology*, vol. 115, No. 7, Jul. 2008, pp. 1196-1202 (7 pages).
Bryant MR, Marchi V, Juhasz T, "Mathematical Models of Picosecond Laser Keratomileusis for High Myopia," *Journal of Refractive Surgery*, vol. 16, No. 2, Mar.-Apr. 2000, pp. 155-162 (9 pages).
Bryant MR, McDonnell PJ, "Constitutive Laws for Biomechanical Modeling of Refractive Surgery," *Journal of Biomechanical Engineering*, vol. 118, Nov. 1996, pp. 473-481 (10 pages).
Buzard KA, Fundingsland BR, "Excimer Laser Assisted in Situ Keratomileusis for Hyperopia," *Journal of Cataract & Refractive Surgery*, vol. 25, Feb. 1999, pp. 197-204 (8 pages).
Charman WN, "The Eye in Focus: Accommodation and Presbyopia," *Clinical and Experimental Optometry*, vol. 91, May 2008, pp. 207-225 (19 pages).
Corbett et al, "Effect of Collagenase Inhibitors on Coreal Haze after PRK", Exp. Eye Res., vol. 72, Issue 3, pp. 253-259, dated Jan. 29, 2001 (7 pages).
Cox CA, Krueger RR, "Monovision with Laser Vision Correction," *Ophthalmology Clinics of North Amermica*, vol. 19, No. 1, Mar. 2006, pp. 71-75 (7 pages).
Doss JD, Albillar JI, "A Technique for the Selective Heating of Corneal Stroma," *Contact & Intraocular Lens Medical Journal*, vol. 6, No. 1, Jan.-Mar. 1980, pp. 13-17 (8 pages).
Elsheikh A, Anderson K, "Comparative Study of Corneal Strip Extensometry and Inflation Tests," *Journal of the Royal Society Interface*, vol. 2, May 2005, pp. 177-185 (10 pages).
Evans BJW, "Monovision: a Review," *Ophthalmic and Physiological Optics*, vol. 27, Jan. 2007, pp. 417-439 (23 pages).
Gasset AR, Kaufman HE, "Thermokeratoplasty in the Treatment of Keratoconus," *American Journal of Ophthalmology*, vol. 79, Feb. 1975, pp. 226-232 (8 pages).
Gloster J, Perkins ES, "The Validity of the Imbert-Flick Law as Applied to Applanation Tonometry," *Experimental Eye Research*, vol. 2, Jul. 1963, pp. 274-283 (10 pages).
Gupta N, Naroo SA, "Factors Influencing Patient Choice of Refractive Surgery or Contact Lenses and Choice of Centre," *Contact Lens & Anterior Eye*, vol. 29, Mar. 2006, pp. 17-23 (7 pages).
Hamilton DR, Hardten DR, Lindstrom RL, "Thermal Keratoplasty," *Cornea*, 2$^{nd}$ Edition, Chapter 167, 2005, pp. 2033-2045 (13 pages).
Hersh PS, "Optics of Conductive Keratoplasty: Implication for Presbyopia Management," *Transactions of the American Ophthalmological Society*, vol. 103, 2005, pp. 412-456 (45 pages).
Hjortdal JO, "Extensibility of the Normo-Hydrated Human Cornea," *Acta Ophthalmologica Scandinavica*, vol. 73, No. 1, Feb. 1995, pp. 12-17 (7 pages).
Hori-Komai Y, Toda I, Asano-Kato N, Tsubota K, "Reasons for Not Performing Refractive Surgery," *Journal of Cataract & Refractive Surgery*, vol. 28, May 2002, pp. 795-797 (3 pages).
Illueca C, Alió JL, Mas D, Ortiz D, Pérez J, Espinosa J, Esperanza S, "Pseudoaccommodation and Visual Acuity with Technovision PresbyLASIK and a Theoretical Simulated Array® Multifocal Intraocular Lens," *Journal of Refractive Surgery*, vol. 24, Apr. 2008, pp. 344-349 (6 pages).
Jain S, Arora I, Azar DT, "Success of Monovision in Presbyopes: Review of the Literature and Potential Applications to Refractive Surgery," *Survey of Ophthalmology*, vol. 40, No. 6, May-Jun. 1996, pp. 491-499 (9 pages).
Jin GJC, Lyle A, Merkley KH, "Laser in Situ Keratomileusis for Primary Hyperopia," *Journal of Cataract & Refractive Surgery*, vol. 31, Apr. 2005, pp. 776-784 (9 pages).
Kaliske M, "A Formulation of Elasticity and Viscoelasticity for Fibre Reinforced Material at Small and Finite Strains," *Computer Methods in Applied Mechanics and Engineering*, vol. 185, 2000, pp. 225-243 (19 pages).

(56) References Cited

OTHER PUBLICATIONS

Llovet F, Galal A, Benitez-del-Castillo J-M, Ortega J, Martin C, Baviera J, "One-Year Results of Excimer Laser in Situ Keratomileusis for Hyperopia," *Journal of Cataract & Refractive Surgery*, vol. 35, Jul. 2009, pp. 1156-1165 (10 pages).
Loarie TM, Applegate D, Kuenne CB, Choi LJ, Horowitz DP, "Use of Market Segmentation to Identify Untapped Consumer Needs in Vision Correction Surgery for Future Growth," *Journal of Refractive Surgery*, vol. 19, No. 5, Sep.-Oct. 2003, pp. 566-576 (12 pages).
Maxwell WA, Lane SS, Zhou F, "Performance of Presbyopia-Correcting Intraocular Lenses in Distance Optical Bench Tests," *Journal of Cataract & Refractive Surgery*, vol. 35, Jan. 2009, pp. 166-171 (6 pages).
McDonald MB, Durrie D, Asbell P, Maloney R, Nichamin L, "Treatment of Presbyopia With Conductive Keratoplasty: Six-Month Results of the 1-Year United States FDA Clinical Trial," *Cornea*, vol. 23, No. 7, Oct. 2004, pp. 661-668 (8 pages).
McDonald MB, "Conductive Keratoplasty: a Radiofrequency-Based Technique for the Correction of Hyperopia," *Transactions of the American Ophthalmological Society*, vol. 103, Dec. 2005, pp. 512-536 (25 pages).
Moriera MD, Garbus JJ, Fasano A, Lee M, Clapham TN, McDonnel PJ, "Multifocal Corneal Topographic Changes With Excimer Laser Photorefractive Keratectomy," *Archives of Ophthalmology*, vol. 110, Jul. 1992, pp. 994-999 (6 pages).
Nash IS, Greene PR, Foster CS, "Comparison of Mechanical Properties of Keratoconus and Normal Corneas," *Experimental Eye Research*, vol. 35, 1982, pp. 413-424 (12 pages).
Newman JM, "Analysis, Interpretation, and Prescription for the Ametropias and Heterophorias," *Borish's Clinical Refraction*, 1998, pp. 776-822 (49 pages).
Pandolfi A, Manganiello F, "A Model for the Human Cornea: Formulation and Numerical Analysis," *Biomechanics and Modeling in Mechanobiology*, vol. 5, Jan. 2006, pp. 237-246 (10 pages).
Pertaub R, Ryan TP, "Numerical Model and Analysis of an Energy-Based System Using Microwaves for Vision Correction," *Proceedings of SPIE*, vol. 7181, Feb. 2009, p. 718105-1 to 718105-14 (14 pages).
Petroll WM, Roy P, Chuong CJ, Hall B, Cavanagh HD, Jester JV, "Measurement of Surgically Induced Corneal Deformations Using Three-Dimensional Confocal Microscopy," *Cornea*, vol. 15, No. 2, Mar. 1996, pp. 154-164 (12 pages).
Pinelli R, Ortiz D, Simonetto A, Bacchi C, Sala E, Alió JL, "Correction of Presbyopia in Hyperopia With a Center-Distance Paracentral-Near Technique Using the Technolas 217Z Platform," *Journal of Refractive Surgery*, vol. 24, May 2008, pp. 494-500 (7 pages).
Pinsky PM, Datye DV, "A Microstructurally-Based Finite Element Model of the Incised Human Cornea," *Journal of Biomechanics*, vol. 24, No. 10, Apr. 1991, pp. 907-922 (15 pages).
Pinsky PM, Datye DV, "Numerical Modeling of Radial, Astigmatic, and Hexagonal Keratotomy," *Refractive and Conical Surgery*, vol. 8, No. 2, Mar.-Apr. 1992, pp. 164-172 (11 pages).
Pinsky PM, van der Heide D, Chernyak D, "Computational Modeling of Mechanical Anisotropy in the Cornea and Sclera," *Journal of Cataract & Refractive Surgery*, vol. 31, Jan. 2005, pp. 136-145 (10 pages).
Riley C, Chalmers RL, "Survey of Contact Lens-Wearing Habits and Attitudes Toward Methods of Refractive Correction: 2002 Versus 2004," *Optometry and Vision Science*, vol. 82, No. 6, Jun. 2005, pp. 555-561 (7 pages).
Rosenbloom A, "New Aged and Old Aged: Impact of the Baby Boomer," *Journal of the American Optometry Association*, vol. 74, No. 4, Apr. 2003, pp. 211-213 (5 pages).
Rutzen AR, Roberts CW, Driller J, Gomez D, Lucas BC, Lizzi FL, Coleman DJ., "Production of Corneal Lesions Using High-Intensity Focused Ultrasound," *Cornea*, vol. 9, No. 4, Oct. 1990, pp. 324-330 (8 pages).
Ryan TP, Pertaub R, Meyers SR, Dresher RP, Scharf R., "Experimental Results of a New System Using Microwaves for Vision Correction," *Proceedings of SPIE*, vol. 7181, Feb. 2009, pp. 718106.1 to 718106.17 (17 pages).
Seiler T, Matallana M, Bende T, "Laser Thermokeratoplasty by Means of a Pulsed Holmium: YAG Laser for Hyperopic Correction," *Refractive and Corneal Surgery*, vol. 6, No. 5, Sep.-Oct. 1990, pp. 335-339 (6 pages).
Seiler T, Matallana M, Sendler S, Bende T, "Does Bowman's Layer Determine the Biomechanical Properties of the Cornea?" *Refractive and Corneal Surgery*, vol. 8, No. 2, Mar.-Apr. 1992, pp. 139-142 (6 pages).
Shin TJ, Vito RP, Johnson LW, McCarey BE, "The Distribution of Strain in the Human Cornea," *Journal of Biomechanics*, vol. 30, No. 5, May 1997, pp. 497-503 (7 pages).
Solomon KD, Fernandez de Castro LE, Sandoval HP, Biber JM, Groat B, Neff KD, Ying MS, French JW, Donnenfeld ED, Lindstrom RL, "LASIK World Literature Review: Quality of Life and Patient Satisfaction," *Ophthalmology*, vol. 116, No. 4, Apr. 2009, pp. 691-701 (11 pages).
Stanley PF, Tanzer DJ, Schallhorn SC, "Laser Refractive Surgery in the United States Navy," *Current Opinion Ophthalmology*, vol. 19, Jul. 2008, pp. 321-324 (4 pages).
Strenk SA, Strenk LM, Koretz JF, "The Mechanism of Presbyopia," *Progress in Retinal Eye Research*, vol. 24, May 2005, pp. 379-393 (15 pages).
Stringer H, Parr J., "Shrinkage Temperature of Eye Collagen," *Nature*, Dec. 1964, p. 1307 (1 page).
Sutton G., Patmore A.L., Joussen A.M., Marshall J., "Mannose 6-Phosphate Reduces Haze Following Excimer Laser Photorefractive Keratectomry," *Lasers and Light*, vol. 7, No. 2/3, 1996, pp. 117-119 (3 pages).
Telandro A., "Pseudo-Accommodation Cornea: a New Concept for Correction of Presbyopia," *Journal of Refractive Surgery*, vol. 20, No. 5, Sep.-Oct. 2004, pp. S714-S717 (5 pages).
Trembly BS, Hashizume N, Moodie KL, Cohen KL, Tripoli NK, Hoopes PJ, "Microwave Thermal Keratoplasty for Myopia: Keratoscopic Evaluation in Porcine Eyes," *Journal of Refractive Surgery*, vol. 17, No. 6, Nov.-Dec. 2001, pp. 682-688 (8 pages).
Trembly BS, Keates RH, "Combined Microwave Heating and Surface Cooling of the Cornea," *IEEE Transactions on Biomedical Engineering*, vol. 38, No. 1, Jan. 1991, pp. 85-91 (8 pages).
Truscott RJ, "Presbyopia Emerging from a Blur Towards an Understanding of the Molecular Basis for this Most Common Eye Condition," *Experimental Eye Research*, vol. 88, Feb. 2009, pp. 241-247 (7 pages).
Uchio E, Ohno S, Kudoh J, Aoki K, Kisielewicz LT, "Simulation Model of an Eyeball Based on Finite Element Analysis on a Supercomputer," *British Journal of Ophthalmology*, vol. 83, Jun. 1999, pp. 1106-1111 (7 pages).
Wang JQ, Zeng YJ, Li XY, "Influence of Some Operational Variables on the Radial Keratotomy Operation," *British Journal of Ophthalmology*, vol. 84, Jan. 2000, pp. 651-6533 (4 pages).
Wollensak, G., et al., "Riboflavin/Ultraviolet-A-Induced Collagen Crosslinking for the Treatment of Keratoconus," *American Journal of Ophthalmology, Ophthalmic Publ.*, Chicago, IL, US, vol. 135, No. 5, May 1, 2003, pp. 620-627 (8 pages).
Zelichowska B, Rę kas M, Stankiewicz A, Cervino A, Montés-Micó R., "Apodized Diffractive Versus Refractive Multifocal Intraocular Lenses: Optical and Visual Evaluation," *Journal of Cataract & Refractive Surgery*, vol. 34, Dec. 2008, pp. 2036-2042 (7 pages).
Morlet N., Minassian D., Dart J., "Astigmatism and the analysis of its surgical correction", Br f Ophthalmol 2001; 85: pp. 1127-1138.
Extended European search report for European Application 08822043.9, dated Jan. 18, 2013 (7 pages).
European Search Report and Written Opinion for EP 08796370.8, European Patent Office, dated May 3, 2011 (7 pages).
International Search Report for PCT/US2010/029806 dated Jun. 1, 2010 (3 pages).
Written Opinion for PCT/US2010/029806 dated Jun. 1, 2010 (6 pages).
International Search Report for PCT/US2010/029791 dated Jun. 1, 2010 (3 pages).

(56) References Cited

OTHER PUBLICATIONS

Written Opinion for PCT/US2010/029791 dated Jun. 1, 2010 (6 pages).

Trembly et al.; Microwave Thermal Keratoplasty for Myopia: Keratoscopic Evaluation in Procine Eyes; Journal of Refractive Surgery; vol. 17; Nov./Dec. 2001; (8 pages).

* cited by examiner

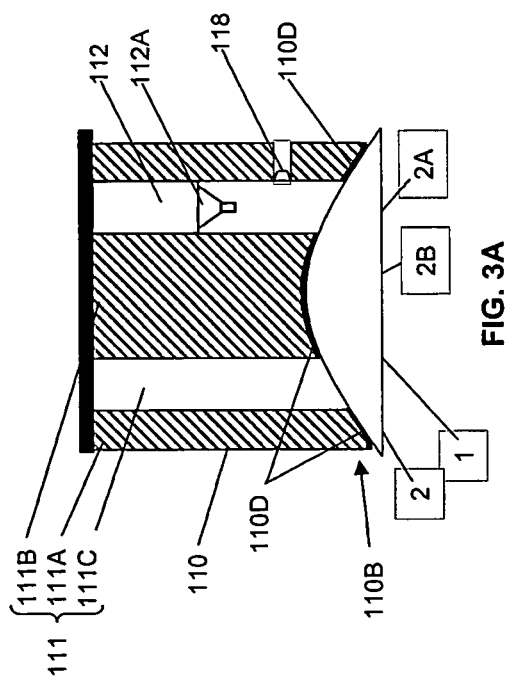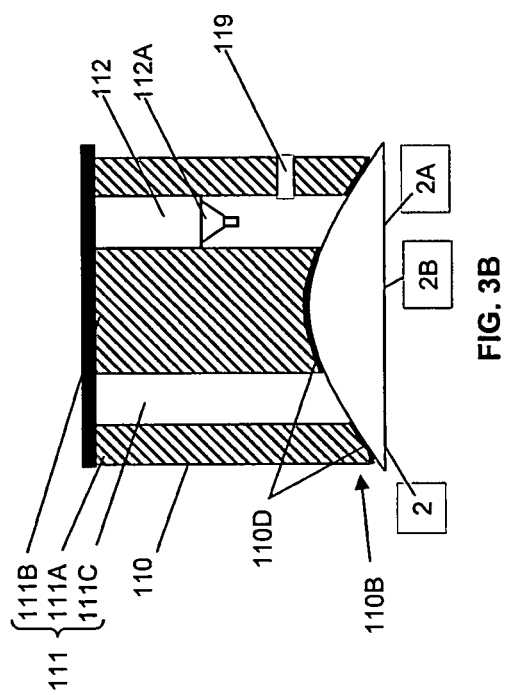

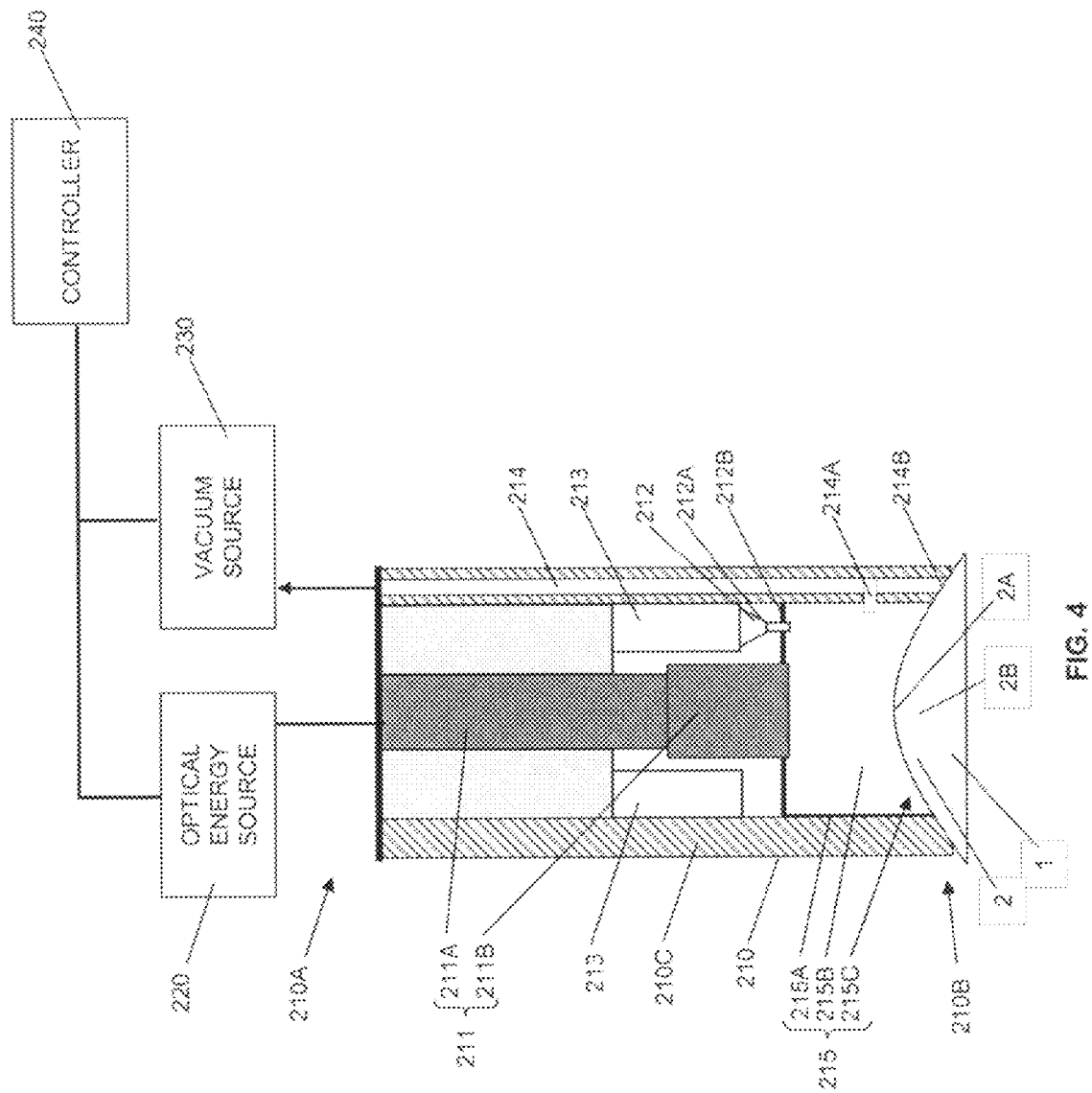

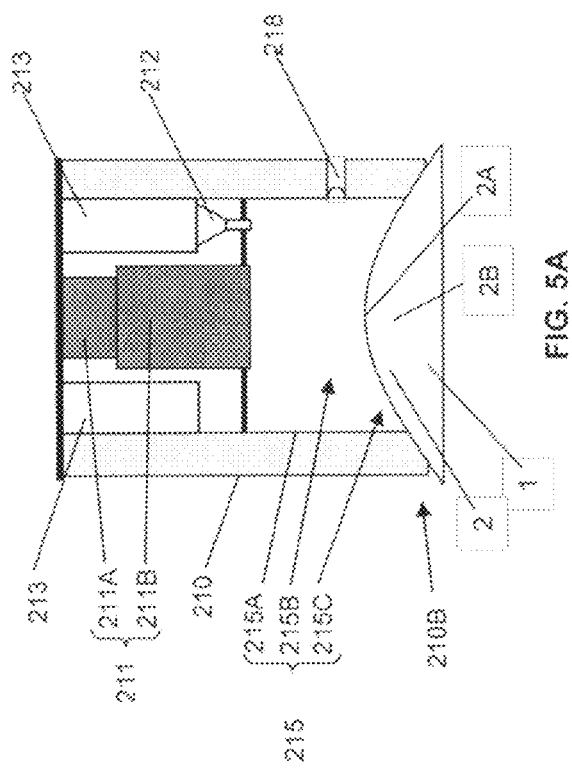
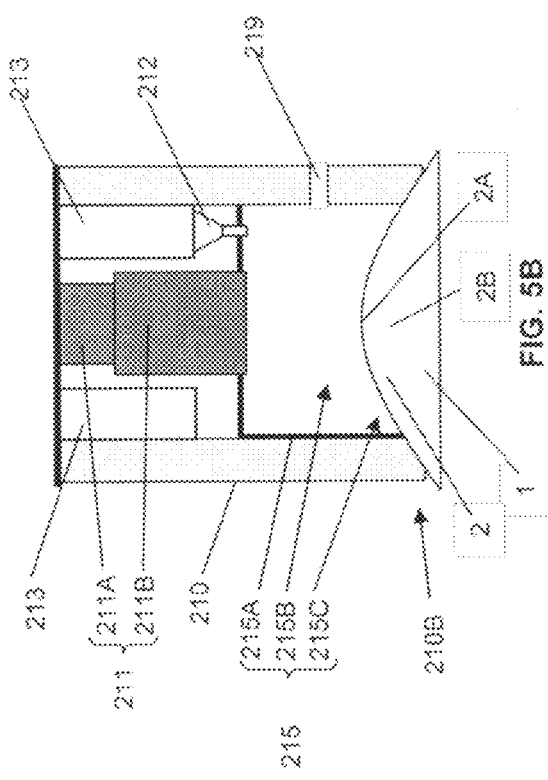

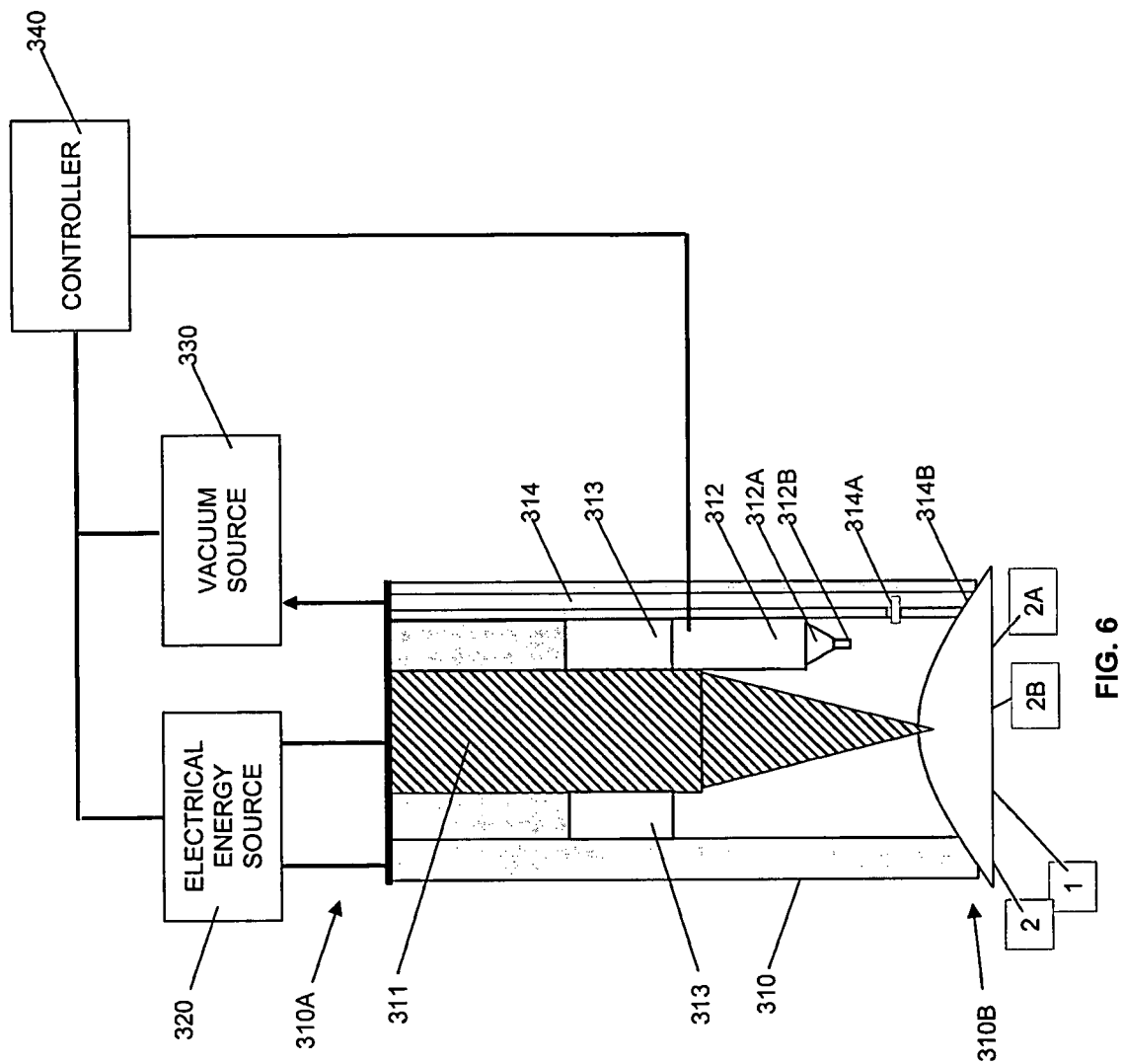

EYE THERAPY SYSTEM

CROSS REFERENCE TO RELATED APPLICATIONS

This application claims the benefit of U.S. Provisional Application No. 60/929,946 filed Jul. 19, 2007, the contents of which are incorporated herein by reference.

BACKGROUND OF THE INVENTION

1. Field of the Invention

The invention pertains to the field of keratoplasty and, more particularly, to thermokeratoplasty and the application of coolant to the eye during thermokeratoplasty.

2. Description of Related Art

A variety of eye disorders, such as myopia, keratoconus, and hyperopia, involve abnormal shaping of the cornea. Keratoplasty reshapes the cornea to correct such disorders. For example, with myopia, the shape of the cornea causes the refractive power of an eye to be too great and images to be focused in front of the retina. Flattening aspects of the cornea's shape through keratoplasty decreases the refractive power of an eye with myopia and causes the image to be properly focused at the retina.

Invasive surgical procedures, such as laser-assisted in-situ keratonomileusis (LASIK), may be employed to reshape the cornea. However, such surgical procedures typically require a healing period after surgery. Furthermore, such surgical procedures may involve complications, such as dry eye syndrome caused by the severing of corneal nerves.

Thermokeratoplasty, on the other hand, is a noninvasive procedure that may be used to correct the vision of persons who have disorders associated with abnormal shaping of the cornea, such as myopia, keratoconus, and hyperopia. Thermokeratoplasty may be performed by applying electrical energy in the microwave or radio frequency (RF) band. In particular, microwave thermokeratoplasty may employ a near field microwave applicator to apply energy to the cornea and raise the corneal temperature. At about 60° C., the collagen fibers in the cornea shrink. The onset of shrinkage is rapid, and stresses resulting from this shrinkage reshape the corneal surface. Thus, application of heat energy in circular or ring-shaped patterns around the pupil may cause aspects of the cornea to flatten and improve vision in the eye. However, devices for thermokeratoplasty generally apply energy through the corneal surface to heat the underlying collagen fibers. Therefore, the maximum temperature can occur at the corneal surface, resulting in possible heat-related injury and damage to the outer layer, known as the epithelium, at the corneal surface. Moreover, devices for thermokeratoplasty may provide inadequate approaches for controlling the depth of heating below the corneal surface and promoting sufficient heating of the targeted collagen fibers while minimizing the application of heat to areas outside the targeted collagen fibers.

SUMMARY OF THE INVENTION

In view of the foregoing, embodiments of the present invention provide a system that selectively applies coolant to the corneal surface to minimize heat-related damage to the corneal surface during thermokeratoplasty and to determine the depth of heating below the corneal surface.

Accordingly, an embodiment of the present invention includes an energy source, a conducting element, a coolant supply, and at least one coolant delivery element. The conducting element is operably connected to the energy source and extends from a proximal end to a distal end. The conducting element directs energy from the energy source to the distal end, which is positionable at an eye. The coolant delivery elements are in communication with the coolant supply and are operable to deliver a micro-controlled pulse of coolant to the distal end.

Another embodiment includes an electrical energy source, an electrical energy conducting element, a coolant supply, and at least one coolant delivery element. The electrical energy conducting element includes two conductors that are separated by a gap of a selected distance and that extend from a proximal end to a distal end. The electrical conducting element, which is operably connected to the electrical energy source, receives, at the proximal end, electrical energy generated by the electrical energy source and directs the electrical energy to the distal end, which is positionable at an eye. The coolant delivery elements are in communication with the coolant supply and are operable to deliver a micro-controlled pulse of coolant to the distal end.

Yet another embodiment includes an optical energy source, an optical energy conducting element, a coolant supply, and at least one coolant delivery element. The optical energy conducting element, which is connected to the optical energy source, extends from a proximal end to a distal end and directs optical energy from the optical energy source to the distal end, which is positionable at an eye. The coolant delivery elements are in communication with the coolant supply and are operable to deliver a micro-controlled pulse of coolant to the distal end.

An additional embodiment includes an energy source, a monopole conductor, a coolant supply, and at least one coolant delivery element. The monopole conductor, which is connected to the energy source, extends from a proximal end to a distal end and contacts, at the distal end, an eye of a body, whereby the body acts as a backplane and the conductor delivers energy to the eye. The coolant delivery elements are in communication with the coolant supply and are operable to deliver a micro-controlled pulse of coolant to the distal end.

A further embodiment includes an energy source, a conducting element, a coolant supply, and a vacuum source. The conducting element, which is operably connected to the energy source, extends from a proximal end to a distal end and directs energy from the energy source to the distal end, which is positionable at the eye. The vacuum source is operable to draw the coolant in a micro-controlled pulse from the coolant supply to the distal end, whereby the pulse of coolant is applied to the eye.

In addition to delivering micro-controlled pulses of coolant, some embodiments may deliver pulses of energy. In particular, the embodiments may employ high power energy to generate heat in a targeted region of the eye in a relatively short amount of time. To minimize unwanted diffusion of heat, the duration of the energy pulse may be shorter than the thermal diffusion time in the targeted region of the eye. In an exemplary application: a first pulse of coolant is delivered to reduce the temperature of the corneal surface; a high power pulse of microwave energy is then applied to generate heat within selected areas of collagen fibers in a mid-depth region; and a second pulse of coolant is delivered in sequence to end further heating effect and "set" the corneal changes that are caused by the energy pulse.

Another embodiment includes an energy conducting element and a vacuum ring. The vacuum ring receives the energy conducting element and creates a vacuum connection with an eye and positions the energy conducting element relative to the eye, whereby the energy conducting element directs the energy to the eye. The energy conducting element may be detachably coupled to the vacuum ring.

The embodiments of the present invention may also employ a controller to control the operation of one or more components or sub-systems. In addition, embodiments may employ pressure relief mechanisms to reduce the pressure introduced by the pulses of coolant into a closed environment. Furthermore, embodiments may also employ a readable use indicator, such as a radio frequency identification (RFID) device, that ensures that elements of the system, particularly those that come into contact with the body and bodily fluids, are disposed of after one use.

These and other aspects of the present invention will become more apparent from the following detailed description of the preferred embodiments of the present invention when viewed in conjunction with the accompanying drawings.

BRIEF DESCRIPTION OF THE DRAWINGS

FIG. 3A illustrates a variation of the embodiment of FIG. 2, which employs a pressure relief valve in place of a vacuum sub-system to reduce pressure created by a pulse of coolant.

FIG. 3B illustrates a variation of the embodiment of FIG. 2, which employs a vent passage in place of a vacuum sub-system to reduce pressure created by a pulse of coolant.

FIG. 4 illustrates an embodiment of the present invention employing an optical energy source.

FIG. 5A illustrates a variation of the embodiment of FIG. 4, which employs a pressure relief valve in place of a vacuum sub-system to reduce pressure created by a pulse of coolant.

FIG. 5B illustrates a variation of the embodiment of FIG. 4, which employs a vent passage in place of a vacuum sub-system to reduce pressure created by a pulse of coolant.

FIG. 6 illustrates an embodiment of the present invention employing a monopole conductor as an energy conducting element.

DETAILED DESCRIPTION

Figure 1:
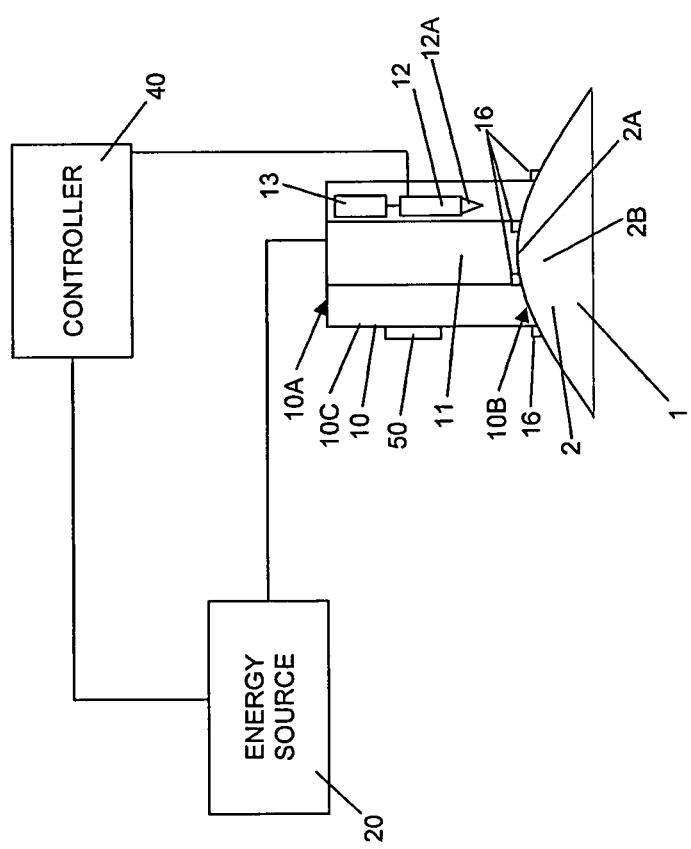
FIG. 1 illustrates a schematic of an embodiment of the present invention.

Referring to FIG. 1, an embodiment of the present invention is schematically illustrated. In particular, FIG. 1 shows an applicator 10 operably connected to an energy source 20. The applicator 10 includes an energy conducting element 11, which extends from the proximal end 10A to the distal end 10B of the applicator 10. The applicator 10 may be connected to the energy source 20 at the proximal end 10A. Operation of the energy source 20 causes energy to be conducted through the energy conducting element 20 and heat to be generated at the distal end 10B. As such, the applicator 10 may be employed to apply heat to a cornea 2 of an eye 1 that is positioned at or near the distal end 10B. In particular, the heat is applied to selected areas of collagen fibers in a mid-depth region 2B of the cornea 2 to shrink the collagen fibers according to a predetermined pattern and reshape the cornea 2, thereby improving vision through the eye 1.

As further illustrated in FIG. 1, the applicator 10 includes at least one coolant delivery element 12 in fluid communication with a coolant supply, or reservoir, 13. The outer surface 10C of the applicator 10 may define a substantially enclosed assembly, especially when the distal end 10A is placed in contact with the corneal surface 2A. As shown in FIG. 1, this enclosed assembly may house the energy conducting element 11, the coolant delivery element 12, and the coolant supply 13. Although the coolant supply 13 in FIG. 1 is positioned within the applicator 10, the coolant supply 13 may be external to the applicator 10 in other embodiments. Moreover, although FIG. 1 shows one coolant delivery element 12, some embodiments may employ more than one coolant delivery element 12 and/or more than one coolant supply 13.

The coolant delivery element 12 delivers a coolant, or cryogen, from the coolant supply 13 to the distal end 10B of the applicator 10. As such, the applicator 10 may be employed to apply coolant to selectively cool the surface 2A of the cornea 2 positioned at the distal end 10B. The delivery of coolant from the coolant delivery element 12 toward the corneal surface 2A, in sequence with the application of heat to the cornea 2, permits the corneal temperature to be increased to cause appropriate shrinkage of the collagen fibers in the targeted mid-depth region 2B and reshape the cornea 2, while also minimizing injury to the outer layer 2A, i.e. the epithelium, of the cornea 2.

A controller 40, as also shown in FIG. 1, may be operably connected to the energy source 20 and/or the coolant delivery element 12. The controller 40 may be employed to control the delivery of energy from the energy source 20 to the applicator 10, thereby determining the magnitude and timing of heat delivered to the cornea 2 positioned at the distal end 10B. In addition, the controller 40 may be employed to determine the amount and timing of coolant delivered from the coolant delivery element 12 toward the corneal surface 2A at the distal end 10B. As described further below, the controller 40 may be employed to selectively apply the heat and the coolant any number of times according to a predetermined or calculated sequence. For instance, the coolant may be applied to the corneal surface 2A before and/or after the application of heat to the cornea 2.

In some embodiments, the coolant delivery element 12 may employ a delivery nozzle 12A and a solenoid valve. The delivery nozzle 12A has an opening 12B directed at the distal end 10B. As is known, a solenoid valve is an electromechanical valve for use with liquid or gas controlled by running or stopping an electrical current through a coil of wire, thus changing the state of the valve. As such, the controller 40 may electronically control the actuation of the solenoid valve to deliver the coolant through the delivery nozzle 12A to the corneal surface 2A. However, other embodiments may employ other types of actuators or alternative techniques for delivering coolant through the delivery nozzle 12A in place of a solenoid valve.

During operation of the embodiment of FIG. 1, the controller 40 may be used to actuate the application of micro-controlled pulses of coolant to the corneal surface 2A before the application of heat to the cornea 2. A pulse, or a spurt, of coolant is applied to the corneal surface 2A for a predetermined short period of time so that the cooling remains generally localized at the corneal surface 2A while the temperature of deeper corneal collagen fibers 2B remains substantially unchanged. Preferably, the pulse is on the order of tens of milliseconds and is less than 100 milliseconds. The delivery of the coolant to the corneal surface is controlled by the controller 40 and may be less than 1 millisecond. Furthermore, the time between the application of the coolant and the application of the heat is also controlled by the controller 40 and may also be less than 1 millisecond. The coolant pulse generally covers an area of the corneal surface 2A that corresponds with the application of heat to the cornea 2. The shape, size and disposition of the cooled region may be varied according to the application.

Advantageously, localized delivery of coolant to the corneal surface 2A before the application of heat to the cornea 2 minimizes the resulting temperature at the corneal surface 2A when the heat is applied, thereby minimizing any heat-induced injury to the corneal surface 2A. In other words, the coolant reduces the temperature of the corneal surface 2A, so that the maximum surface temperature achieved at the corneal surface 2A immediately after heat exposure is also reduced by a similar magnitude when compared to a case where no coolant is applied prior to heat exposure. Without the application of coolant, the temperature at the corneal surface 2A rises immediately after heat exposure with persistent surface heating resulting from a slow dissipation of heat trapped near the surface-air interface.

Although temperatures observed at the corneal surface 2A immediately after heat exposure are lowered by the application of coolant before exposure, a delayed thermal wave may arrive at the corneal surface 2A after exposure as the heat generated in the corneal areas 2B below the surface 2A diffuses toward the cooled surface 2A. The heat transfer from the corneal surface 2A to the surrounding air is likely to be insignificant, because air is an excellent thermal insulator. With no cooling after the application of heat, heat diffusing away from the areas 2B beneath the corneal surface 2A builds up near the corneal surface 2A and produces an elevated surface temperature that may persist after the application of heat. Although the heat that builds up near the corneal surface 2A may eventually dissipate through thermal diffusion and cooling via blood perfusion, such dissipation may take several seconds. More immediate removal of this heat by additional application of coolant minimizes the chances for heat-related injury to the corneal surface 2A. Thus, embodiments of the present invention may employ not only a pulse of coolant immediately prior to heat exposure, but also one or more pulses of coolant thereafter. Accordingly, in further operation of the embodiment of FIG. 1, the controller 40 may also be used to apply micro-controlled pulses of coolant after the applicator 10 applies heat to the cornea 2. This application of coolant rapidly removes heat which diffuses from the mid-depth corneal region 2B to the corneal surface 2A.

When the coolant delivery element 12 delivers the pulse of coolant to the corneal surface 2A, the coolant on the corneal surface 2A draws heat from the surface 2A, causing the coolant to evaporate. In general, coolant applied to the surface 2A creates a heat sink at the surface 2A, resulting in the removal of heat before, during, and after the application of heat to the cornea 2. The heat sink persists for as long as the liquid cryogen remains on the surface 2A. The heat sink can rapidly remove the trapped heat at the surface 2A without cooling the collagen fibers in the region 2B. A factor in drawing heat out of the cornea 2 is the temperature gradient that is established near the surface 2A. The steeper the gradient, the faster a given quantity of heat is withdrawn. Thus, the application of the coolant attempts to produce a large surface temperature drop as quickly as possible.

Because the cooled surface 2A provides a heat sink, the amount and duration of coolant applied to the corneal surface 2A affects the amount of heat that passes into and remains in the region underlying the corneal surface 2A. Thus, controlling the amount and duration of the cooling provides a way to control the depth of corneal heating, promoting sufficient heating of targeted collagen fibers in the mid-depth region 2B while minimizing the application of heat to regions outside the targeted collagen fibers.

In general, dynamic cooling of the corneal surface 2A may be optimized by controlling: (1) the duration of the cooling pulse(s); (2) the quantity of coolant deposited on the corneal surface 2A so that the effect of evaporative cooling can be maximized; and (3) timing of dynamic cooling relative to heat application.

In some embodiments, the coolant may be the cryogen tetrafluoroethane, $C_2H_2F_4$, which has a boiling point of about −26.5° C. and which is an environmentally compatible, non-toxic, nonflammable freon substitute. The cryogenic pulse released from the coolant delivery element 12 may include droplets of the cryogen cooled by evaporation as well as mist formed by adiabatic expansion of vapor.

In general, the coolant may be selected so that it provides one or more of the following: (1) sufficient adhesion to maintain good surface contact with the corneal surface 2A; (2) a high thermal conductivity so the corneal surface 2A may be cooled very rapidly prior to heat application; (3) a low boiling point to establish a large temperature gradient at the surface; (4) a high latent heat of vaporization to sustain evaporative cooling of the corneal surface 2A after laser exposure; and (5) no adverse health or environmental effects. Although the use of tetrafluoroethane may satisfy the criteria above, it is understood that embodiments of the present invention are not limited to a particular cryogen and that other coolants may be employed to achieve similar results. For instance, in some embodiments, other liquid coolants with a boiling temperature of below approximately body temperature, 37° C., may be employed. Furthermore, the coolant does not have to be a liquid, but in some embodiments, may have a gas form. As such, the pulse of coolant may be a pulse of cooling gas. For example, the coolant may be nitrogen ($N_2$) gas or carbon dioxide ($CO_2$) gas.

Figure 2:
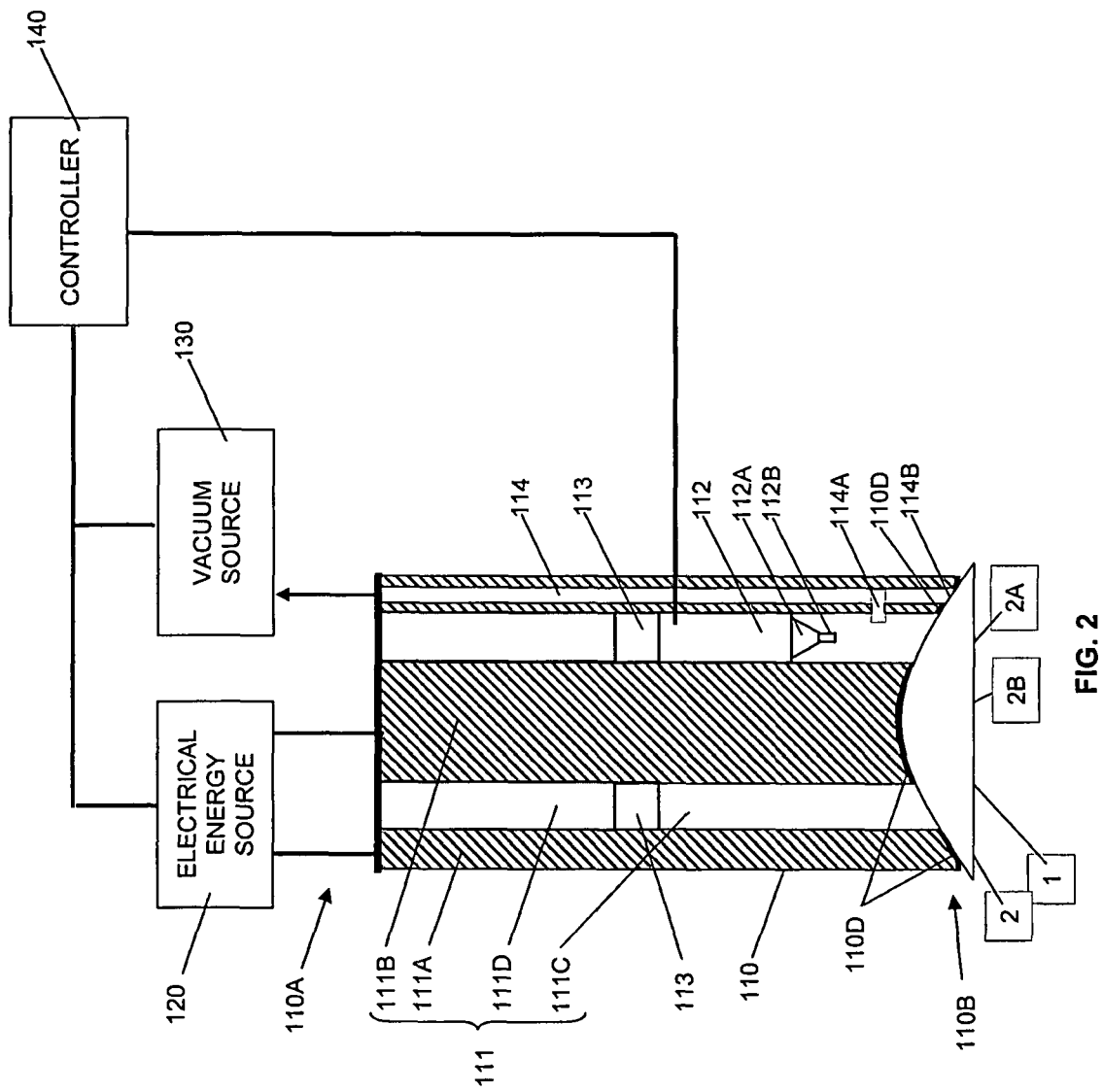
FIG. 2 illustrates an embodiment of the present invention employing a microwave energy source.

Referring now to the cross-sectional view illustrated in FIG. 2, an embodiment of the present invention employs an applicator 110. The applicator 110 includes an electrical energy conducting element 111, a micro-controlled coolant delivery system 112, as well as a coolant supply 113.

The electrical energy conducting element 111 is operably connected to an electrical energy source 120, for example, via conventional conducting cables. The electrical energy conducting element 111 extends from a proximal end 110A to a distal end 110B of the applicator 110. The electrical energy conducting element 111 conducts electrical energy from the source 120 to the distal end 110B to apply heat energy to a cornea 2, which is positioned at the distal end 110B. In particular, the electrical energy source 120 may include a microwave oscillator for generating microwave energy. For example, the oscillator may operate at a microwave frequency range of 500 MHz to 3000 MHz, and more specifically at a frequency of around 2450 MHz which has been safely used in other applications. As used herein, the term "microwave" corresponds to a frequency range from about 10 MHz to about 10 GHz.

As further illustrated in FIG. 2, the electrical energy conducting element 111 may include two microwave conductors 111A and 111B, which extend from the proximal end 110A to the distal end 110B of the applicator 110. In particular, the conductor 111A may be a substantially cylindrical outer conductor, while the conductor 111B may be a substantially cylindrical inner conductor that extends through an inner passage extending through the conductor 111A. With the inner passage, the conductor 111A has a substantially tubular shape. The inner and the outer conductors 111A and 111B may be formed, for example, of aluminum, stainless steel, brass, copper, other metals, metal-coated plastic, or any other suitable conductive material.

With the concentric arrangement of conductors 111A and 111B, a substantially annular gap 111C of a selected distance is defined between the conductors 111A and 111B. The annular gap 111C extends from the proximal end 110A to the distal end 110B. A dielectric material 111D may be used in portions of the annular gap 111C to separate the conductors 111A and 111B. The distance of the annular gap 111C between conductors 111A and 111B determines the penetration depth of microwave energy into the cornea 2 according to established microwave field theory. Thus, the microwave conducting element 111 receives, at the proximal end 110A, the electrical energy generated by the electrical energy source 120, and directs microwave energy to the distal end 111B, where the cornea 2 is positioned.

The outer diameter of the inner conductor 111B is preferably larger than the pupil. In general, the outer diameter of the inner conductor 111B may be selected to achieve an appropriate change in corneal shape, i.e. keratometry, induced by the exposure to microwave energy. Meanwhile, the inner diameter of the outer conductor 111A may be selected to achieve a desired gap between the conductors 111A and 111B. For example, the outer diameter of the inner conductor 111B ranges from about 2 mm to about 10 mm while the inner diameter of the outer conductor 111A ranges from about 2.1 mm to about 12 mm. In some embodiments, the annular gap 111C may be sufficiently small, e.g., in a range of about 0.1 mm to about 2.0 mm, to minimize exposure of the endothelial layer of the cornea (posterior surface) to elevated temperatures during the application of heat by the applicator 110.

As shown in FIG. 2, the micro-controlled coolant delivery system 112 as well as the coolant supply 113 may be positioned within the annular gap 111C. Although FIG. 2 may illustrate one coolant delivery system 112, the applicator 110 may include a plurality of coolant delivery systems 112 arranged circumferentially within the annular gap 111C. The coolant supply 113 may be an annular container that fits within the annular gap 111C, with the coolant delivery element 112 having a nozzle structure 112A extending downwardly from the coolant supply 113 and an opening 112B directed toward the distal end 110B.

The micro-controlled coolant delivery system 112, which is in fluid communication with the coolant supply 113, may operate in a manner similar to the coolant delivery system 12 in FIG. 1. In other words, pulses of coolant, or cryogen, from the coolant supply 113 are preferably applied to the corneal surface 2A before and after energy is applied to the cornea 2 with the electrical energy source 120 and the electrical energy conducting element 111.

As described previously, the controller 140 may be employed to selectively apply the heat and the coolant pulses any number of times according to any predetermined or calculated sequence. In addition, the heat and the pulses of coolant may be applied for any length of time. Furthermore, the magnitude of heat being applied may also be varied. Adjusting such parameters for the application of heat and pulses of coolant determines the extent of changes that are brought about within the cornea 2. Of course, as discussed, embodiments of the present invention attempt to limit the changes in the cornea 2 to an appropriate amount of shrinkage of selected collagen fibers. When employing microwave energy to generate heat in the cornea 2, for example with the applicator 110, the microwave energy may be applied with low power (of the order of 40 W) and in long pulse lengths (of the order of one second). However, other embodiments may apply the microwave energy in short pulses. In particular, it may be advantageous to apply the microwave energy with durations that are shorter than the thermal diffusion time in the cornea. For example, the microwave energy may be applied in pulses having a higher power in the range of 500 W to 3 KW and a pulse duration in the range of about 10 milliseconds to about one second. Thus, when applying the coolant pulses before and after the application of heat as discussed previously: a first pulse of coolant is delivered to reduce the temperature of the corneal surface 2A; a high power pulse of microwave energy is then applied to generate heat within selected areas of collagen fibers in a mid-depth region 2B; and a second pulse of coolant is delivered in sequence to end further heating effect and "set" the corneal changes that are caused by the energy pulse. The application of energy pulses and coolant pulses in this manner advantageously reduces the amount to heat diffusion that occurs and minimizes the unwanted impact of heating and resulting healing processes on other eye structures, such as the corneal endothelium. Moreover, this technique promotes more permanent and stable change of the shape of the cornea 2 produced by the heat. Although the application of high powered energy in short pulses has been described with respect to the delivery of microwave energy, a similar technique may be applied with other types of energy, such as optical energy or electrical energy with radio frequency (RF) wavelengths described further below.

Referring again to FIG. 2, at least a portion of each of the conductors 111A and 111B may be covered with an electrical insulator to minimize the concentration of electrical current in the area of contact between the corneal surface 2A and the conductors 111A and 111B. In some embodiments, the conductors 111A and 111B, or at least a portion thereof, may be coated with a material that can function both as an electrical insulator as well as a thermal conductor. A dielectric layer 110D may be employed along the distal end 111B of the applicator 110 to protect the cornea 2 from electrical conduction current that would otherwise flow into the cornea 2 via conductors 111A and 111B. Such current flow may cause unwanted temperature effects in the cornea 2 and interfere with achieving a maximum temperature within the collagen fibers in the mid-depth region 2B of the cornea 2. Accordingly, the dielectric layer 110D is positioned between the conductors 111A and 111B and the cornea 2. The dielectric layer 110D may be sufficiently thin to minimize interference with microwave emissions and thick enough to prevent superficial deposition of electrical energy by flow of conduction current. For example, the dielectric layer 110D may be a biocompatible material, such as Teflon, deposited to a thickness of about 0.002 inches. In general, an interposing layer, such as the dielectric layer 110D, may be employed between the conductors 111A and 111B and the cornea 2 as long as the interposing layer does not substantially interfere with the strength and penetration of the microwave radiation field in the cornea 2 and does not prevent sufficient penetration of the microwave field and generation of a desired heating pattern in the cornea 2.

During operation, the distal end 110B of the applicator 110 as shown in FIG. 2 is positioned on or near the corneal surface 2A. Preferably, the applicator 10 makes direct contact with the corneal surface 2A. In particular, such direct contact positions the conductors 111A and 111B at the corneal surface 2A (or substantially near the corneal surface 2A if there is a thin interposing layer between the conductors 111A and 111B and the corneal surface 2A). Accordingly, direct contact helps ensure that the pattern of microwave heating in the corneal tissue has substantially the same shape and dimension as the gap 111C between the two microwave conductors 111A and 111B. An annulus is a preferred heating pattern because the inner diameter of the heated annulus can be selected to be sufficiently large so as to avoid heating the central cornea overlying the pupil.

The advantages of direct contact between the applicator 10 and the corneal surface 2A may be reduced by the presence of a layer of fluid coolant which may exist therebetween. Rather than creating an annular heating pattern with dimensions equal to that of the gap between the conductors 111A and 111B, the presence of such a fluid layer may cause a less desirable circle-shaped microwave heating pattern in the cornea 2 with a diameter less than that of the inner conductor 111B. Therefore, embodiments of the present invention do not require a flow of coolant or a cooling layer to exist over the corneal surface 2A during the application of energy to the cornea 2. In particular, the short pulses from the coolant delivery element 112 may apply a coolant that evaporates from the corneal surface before the application of the microwave energy and thus does not create a fluid layer that would interfere with the desired microwave pattern.

Embodiments may employ a vacuum passageway 114 operably connected to a vacuum source 130. The vacuum passageway 114 may have an opening 114A that is positioned near the corneal surface 2A and opens to the interior of the applicator 110. The vacuum source 130 may be used to draw any coolant, or unwanted fluid layer, from the corneal surface 2A before the microwave energy is applied to the cornea 2. In this case, the vacuum source 130 also draws the fluid to a waste receptacle (not shown).

The application of coolant and the subsequent evaporation of coolant may cause the pressure to increase within the applicator 110. In particular, the applicator 110 may have an outer surface 110C that may define a substantially enclosed assembly, especially when the distal end 110B is placed in contact with the corneal surface 2A. As shown in FIG. 2, the substantially enclosed assembly contains the electrical conducting element 111, the coolant delivery element 112, the coolant supply 113, as well as the vacuum passageway 114. The pressure is more likely to increase within such an enclosed assembly. As the applicator 110 may be in contact with the corneal surface 2A, the resulting pressure may act against the corneal surface 2A. Therefore, to minimize the effects of this pressure on the corneal surface 2A, embodiments may employ a pressure relief mechanism for removing excess pressure that may occur in the applicator 110.

In addition to the functions of the vacuum passageway 114 discussed previously, the vacuum passageway 114 with opening 114A may also act as a pressure relief mechanism for the applicator 110. As such, the pressure in the applicator 110 may be lowered by activating the vacuum source 130. Alternatively, as shown in FIG. 3A, the applicator 110 may include any type of pressure relief valve 118 that opens up the interior of the applicator 110 to the environment external to the applicator 110 when the pressure in the applicator 110 rises to a certain level. As another alternative shown in FIG. 3B, the applicator 110 may simply employ a vent passage 119 that places the interior of the applicator 110 in communication with the environment external to the applicator 110, in which case the pressure interior will generally be in equilibrium with the external area.

As FIG. 2 further illustrates, the vacuum passageway 114 also passes through the dielectric material 110D and has an opening 114B at the distal end 110B. While the opening 114A opens to the interior of the applicator 110, the opening 114B opens to the corneal surface 2A which is positioned at the distal end 110B. With the opening 114B positioned at the corneal surface 2A, the vacuum passageway 114 with the vacuum source 140 helps the applicator 110 to maintain a fixed position relative to cornea 2 during treatment. The vacuum source 130 may apply a controlled amount of suction to the corneal surface 2A to ensure that the applicator surface at the distal end 110B has a firm and even contact with the cornea 2.

Referring now to the cross-sectional view illustrated in FIG. 4, another embodiment of the present invention employs an applicator 210, which includes an optical energy conducting element 211, a micro-controlled coolant delivery system 212, as well as a coolant supply 213.

The optical energy conducting element 211 is operably connected to an optical energy source 220, for example, via conventional optical fiber. The optical energy source 220 may include a laser, a light emitting diode, or the like. The optical energy conducting element 211 extends to the distal end 210B from the proximal end 210A, where it is operably connected with the optical source 220. The optical energy conducting element includes an optical fiber 211A. Thus, the optical fiber 211A receives optical energy from the optical energy source 220 at the proximal end 210A and directs the optical energy to the distal end 210B, where the cornea 2 of an eye 1 is positioned. A controller 240 may be operably connected to the optical energy source 220 to control the delivery, e.g. timing, of the optical energy to the optical conducting element 211. The optical energy conducting element 211 irradiates the cornea 2 with the optical energy and generates heat for appropriately shrinking collagen fibers in the mid-depth region 2B of the cornea 2. As also illustrated in FIG. 4, the optical conducting element may optionally include an optical focus element 212B, such as a lens, to focus the optical energy and to determine the pattern of irradiation for the cornea 2.

As FIG. 4 illustrates, the coolant delivery system 212 may be positioned adjacent to the optical energy conducting element 211. The coolant delivery system 212, which is in fluid communication with the coolant supply 213, delivers micro-controlled pulses of coolant, or cryogen, from the coolant supply 213 to the corneal surface 2A. Such pulses of coolant may be applied before and/or after energy is applied to the cornea 2 with the optical energy source 220 and the optical energy conducting element 211.

FIG. 4 further illustrates another technique for delivering pulses of coolant to the corneal surface 2A. In particular, the pulse of coolant may be drawn from the coolant delivery element 212 by creating an area of low pressure at or near the distal end 210B, where the corneal surface 2A is positioned. As shown in FIG. 4, the applicator 210 may have a vacuum passageway 214, such as a tube structure, which is connected to the vacuum source 230. The vacuum passageway 214 has an opening 214A which is positioned at or near the distal end 210B to create the area of low pressure. To enhance the applicator's ability to create this low pressure area, the applicator 210, as illustrated in FIG. 4, may include a contact element 215 that defines a small enclosure in which the area of low pressure can be created.

In particular, FIG. 4 shows that the applicator 210 includes a contact element 215 at the distal end 210B which makes contact with the corneal surface 2A. The contact element 215 has a housing 215A with a cavity 215B. The housing 215A has an opening 215C at the distal end 210B of the applicator 210, so that the cavity 215B is exposed to the distal end 210B. As such, the contact element 215 forms an enclosure over the cornea 2 when it is positioned over the cornea 2. As shown further in FIG. 4, the nozzle structure 212A of the coolant delivery element 212 is received by the contact element 215 and the opening 212B opens to the cavity 215B. In some embodiments, the coolant delivery system 212 simply places the coolant supply in communication with the contact element 215 via structure 212A. While one coolant delivery element 212 is illustrated in FIG. 4, it is understood that more than one coolant delivery element 212 may be employed by the applicator 210. The vacuum passageway 214 is also received by the contact element, where the opening 214A opens to the cavity 215B. Accordingly, when the contact element 215 is positioned over the corneal surface 2A to form an enclosure, the vacuum source 240 may be operated to create a near vacuum or low pressure in the cavity 215B, which in turn draws the coolant through the nozzle structure 212A toward the corneal surface 2A positioned at the opening 215C. The controller 240 may be operably connected to control the vacuum source 240 to cause micro-controlled pulses of coolant to be drawn from the coolant delivery element 212.

Of course, it is understood that in other embodiments, the contact element 215 may be employed with a coolant delivery element 212 that employs a solenoid valve, or other actuator, and does not require the vacuum source 230. As such, the controller 140 may electronically control the solenoid valve, or other actuator, to deliver the coolant to the corneal surface 2A.

The application of coolant to the corneal surface 2A and the subsequent evaporation of coolant may cause the pressure to increase within the cavity 215A of the contact element 215. As the contact element 215 is positioned against the corneal surface 2A, the resulting pressure may act against the corneal surface 2A. Therefore, to minimize the effects of this pressure on the corneal surface 2A, embodiments may employ a pressure relief mechanism for removing excess pressure that may occur in the applicator 210.

In addition to providing a way to initiate micro-controlled pulses of coolant, the vacuum passageway 214 may also act as a pressure relief mechanism for the applicator 210. As such, the pressure in the applicator 210 may be lowered by activating the vacuum source 230. Alternatively, as shown in FIG. 5A, the applicator 210 may include any type of pressure relief valve 218 that opens up the interior of the applicator 210 to the environment external to the applicator 210 when the pressure in the applicator 210 rises to a certain level. As another alternative shown in FIG. 5B, the applicator 210 may simply employ a vent passage 219 that places the interior of the applicator 210 in communication with the environment external to the applicator 210, in which case the interior pressure will generally be in equilibrium with the external area. Of course, as there is no vacuum source shown in the embodiments of FIGS. 5A and 5B, the coolant delivery element 212 requires another element such as a solenoid valve, or other actuator, to deliver the pulses of coolant.

As further shown in FIG. 4, the contact element 215 also receives the optical conducting element 211, so that the applicator 210 can deliver the optical energy from the optical energy source 220 to the cornea 2 at the distal end 210B. FIG. 4 shows that the optical focus element 211B is connected to the contact element 215.

Advantageously, the contact element 215 may act as an additional heat sink for drawing heat from the corneal surface 2A, as the contact element 215 is in direct contact with the corneal surface 2A. In particular, the contact element may be formed from a heat conducting material, such as a metal. In general, other heat sinks, such as metal applicator walls 410C, may be employed with embodiments of the present invention to provide further heat transfer from the corneal surface 2A.

As FIG. 4 further illustrates, the vacuum passageway 214 also has an opening 214B at the distal end 210B. While the opening 214A opens to the cavity 215B of the contact element 215, the opening 214B opens to the corneal surface 2A which is positioned at the distal end 110B. With the opening 214B positioned at the corneal surface 2A, the vacuum passageway 214 with the vacuum source 240, the applicator 210 to maintain a fixed position relative to cornea 2 during treatment. The vacuum source 230 may apply a controlled amount of suction via opening 214B to the corneal surface 2A to ensure that applicator surface at the distal end 210B has a firm and even contact with the cornea 2.

Referring now to the cross-sectional view illustrated in FIG. 6, another embodiment of the present invention is illustrated. In particular, the embodiment of FIG. 6 illustrates an applicator 310 which employs a monopole conducting element 311 for conducting energy to the cornea 2.

The monopole conducting element 311 is operably connected to an electrical energy source 320, which may provide a radio frequency (RF) electrical energy. The monopole 311 extends to the distal end 310B from the proximal end 310A, where it is operably connected with the electrical energy source 320. The monopole conducting element 311 may have a needle-like shape at the distal end 310B, which is designed to contact or penetrate the cornea 2. When the applicator is positioned to place the monopole 311 into contact with the eye 1, the eye 1, i.e. the body, acts as a backplane to complete the circuit. Accordingly, the monopole 311 may receive the electrical energy generated at the electrical energy source 320 and conduct electrical energy to the cornea 2 of an eye 1. As a result, heat is generated within the cornea 2 to shrink selected collagen fibers in the mid-depth region 2B of the cornea 2 and to reshape the cornea 2. A controller 340 may be operably connected to the electrical energy source 320 to control the delivery, e.g. timing, of the electrical energy to the monopole 311.

Other aspects of the embodiment of FIG. 6 are similar to the embodiments described previously. In particular, as FIG. 6 illustrates, the applicator 310 also employs a micro-controlled coolant delivery system 312 as well as a coolant supply 313. The micro-controlled coolant delivery system 312 is positioned adjacent to the monopole 311. The coolant delivery element 312 may employ a nozzle structure 312A with an opening 312B directed at the distal end 310B. A solenoid valve, or other actuator, may be employed to create the pulses of coolant. The controller 340 may electronically control the solenoid valve, or other actuator, to deliver the coolant to the corneal surface 2A. As such, the micro-controlled coolant delivery system 312, which is in fluid communication with the coolant supply 313, operates in a manner similar to the coolant delivery system 12 in FIG. 1. In other words, pulses of coolant, or cryogen, from the coolant supply 313 are preferably applied to the corneal surface 2A before and after the energy is applied to the cornea 2.

As also shown in FIG. 6, the applicator 320 may include a vacuum passageway 314 with an opening 314A positioned at or near the distal end 310B. The vacuum passageway 314 is operably connected to a vacuum source 330, which may be controlled by the controller 340. Similar to other embodiments described previously, the vacuum source 340 and the vacuum passageway 314 may be operated to relieve pressure created by the delivery of coolant from the coolant delivery element 312. Alternatively, a pressure relief valve or a vent passage may be employed to act as the pressure relief element, in a manner similar to embodiments described previously.

In addition, as further shown in FIG. 6, the vacuum passageway 314 may also have an opening 314B that opens to the corneal surface 2A which is positioned at the distal end 310B. With the opening 314B positioned at the corneal surface 2A, the vacuum passageway 314 with the vacuum source 340 creates suction between the applicator 110 and the corneal surface 2A to maintain the applicator 310 in a fixed position relative to cornea 2 during treatment.

In general, any arrangement of vacuum openings operably connected to a vacuum source may be employed to keep embodiments of the present invention in position over the corneal surface during treatment. For example, FIG. 7A shows an applicator 410 which is positioned over the cornea 2 with a vacuum ring 417. Like the applicators described above, the applicator 410 includes an energy conducting element 411, such as those discussed previously, which extends from the proximal end 410A to the distal end 410B of the applicator 410. The energy conducting element 411 is operably connected to an energy source 420 at the proximal end 410A. Operation of the energy source 420 causes energy to be conducted through the energy conducting element 420 and heat to be generated at the distal end 410B. As such, the vacuum ring 417 positions the distal end 410B of the applicator 410 over the cornea 2 to enable the energy conducting element 411 to generate heat at the cornea 2. In particular, the heat is applied to targeted collagen fibers in a mid-depth region 2B of the cornea 2, thereby shrinking the collagen fibers and reshaping the cornea 2 to improve vision through the eye 1.

Figure 7B:
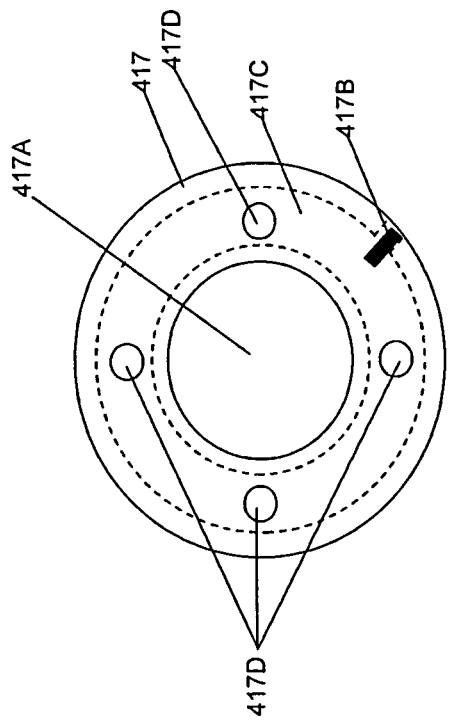
FIG. 7B illustrates the vacuum ring employed in the embodiment of FIG. 7A.
Figure 7A:
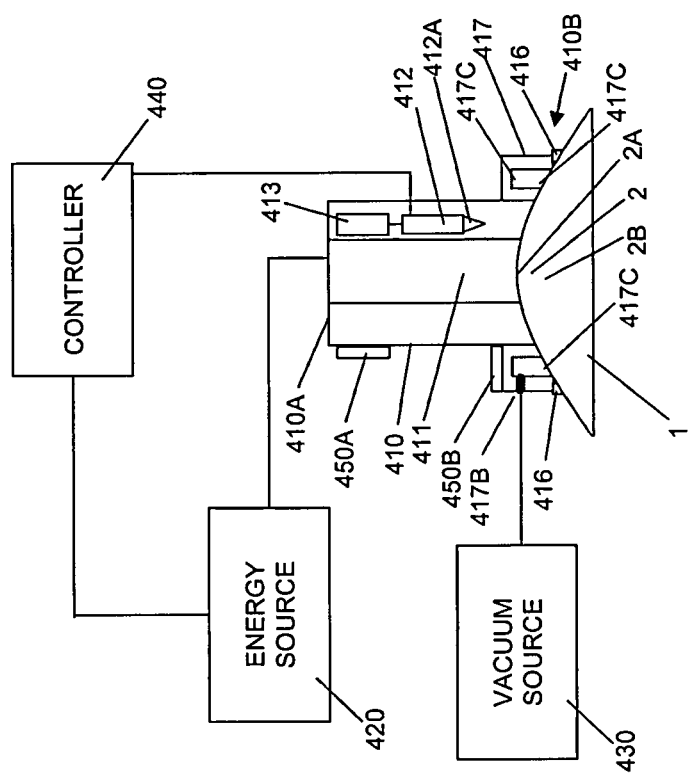
FIG. 7A illustrates an embodiment of the present invention employing a vacuum ring to position an applicator over an eye surface.

As shown further in FIGS. 7A and 7B, the vacuum ring 417 has a substantially annular structure and receives the energy conducting element 411 coaxially through a ring passage 417A. The vacuum ring 417 creates a vacuum connection with the corneal surface 2A to fix the energy conducting element 411 to the corneal surface 2A. The vacuum ring 417 may include an interior channel 417C which is operably connected to the vacuum source 430 via connection port 417B. The vacuum ring 417 may also include a plurality of openings 417D which open the interior channel 417B to the corneal surface 2A. Therefore, when the openings 417D are positioned in contact with the corneal surface 2A and the vacuum source 430 is activated to create a near vacuum or low pressure within the interior channel 417C, the openings 417D operate to suction the vacuum ring 417 and the applicator 410 to the corneal surface 2A. In this case, the vacuum source 430 may be a syringe or similar device.

In some embodiments, the energy conducting element 411 and the vacuum ring 417 may be separate components which may be detachably coupled to each other. Thus, as shown in FIG. 7A, a separate energy conducting element 411 may be slidingly received by the vacuum ring 417 into the coaxial position. Any coupling technique, such as a mechanical attachment, may be employed to keep the energy conducting element 411 stably positioned within the vacuum ring 417. The vacuum ring 417 may be positioned on the corneal surface 2A before it receives the energy conducting element 411, or alternatively, the electrical conducting element 411 may be combined with the vacuum ring 417 before the combination is positioned on the corneal surface 2A.

In alternative embodiments, the energy conducting element 411 and the vacuum ring 417 may be non-detachably fixed to each other.

Other aspects of the embodiment of FIG. 7 are similar to the embodiments described previously. In particular, as FIG. 7 illustrates, the applicator 410 also employs a micro-controlled coolant delivery system 412 as well as a coolant supply 413. The coolant delivery element 412 may employ a nozzle structure 412A with an opening 412B directed at the distal end 410B. A solenoid valve, or other actuator, may be employed to create the pulses of coolant. The controller 440 may electronically control the solenoid valve, or other actuator, to deliver the coolant to the corneal surface 2A. As such, the micro-controlled coolant delivery system 412, which is in fluid communication with the coolant supply 413, operates in a manner similar to the coolant delivery system 12 in FIG. 1. In other words, pulses of coolant, or cryogen, from the coolant supply 413 are preferably applied to the corneal surface 2A before and after the energy is applied to the cornea 2.

The embodiments described herein may all employ sensors to measure physical variables of the eye. For example, in one embodiment, FIG. 1 depicts a plurality of sensors 16 which are discretely positioned at and about the distal end 10B of the applicator 10. The sensors may be operably connected to the controller 40 (not shown) to allow the data to be stored and/or communicated to operators. As a further example, the embodiment of FIGS. 7A and 7B employs an arrangement of sensors 416 on the vacuum ring 417 as the vacuum ring 417 makes direct contact with the corneal surface 2A. In other embodiments, sensors may be more broadly incorporated into a surface at the distal end of the applicator, such as the dielectric layer 110D in FIG. 2. Typically, the sensors are placed in contact with the cornea and provide measurements for various areas of the cornea. In general, the sensors may include devices that are formed as parts of the applicator and/or external devices that are separate from the applicator. The sensors may be microelectronic devices, including, but not limited to, infrared detectors that measure temperature, thin film or microelectronic thermal transducers, mechanical transducers such as a piezoresistive or piezoelectric devices, or force-sensitive quartz resonators that quantify corneal elongation or internal pressure.

In general, the sensors may provide information that is used to prepare the systems before treatment, provide feedback during treatment to ensure proper application of treatment, and/or measure the results of the treatment.

The cornea and eye have one or more variable physical properties that may be affected by the application of energy and the resulting increase in temperature. The sensors may directly or indirectly measure these physical variables and provide a sensor signal to processing circuitry, such as the controllers 40, 140, 240, and 340 described above. The controller may analyze the measurements to determine if and when the treatment has achieved the desired effects. Processing circuitry may also generate a stop signal that terminates treatment when a specified physical variable achieves a predetermined value or falls within a predetermined range. In some embodiments, to avoid thermal damage to the corneal epithelium, and the endothelium, program instructions for the controller may include a safety mechanism that generates a stop signal when the application of heat energy exceeds certain parameters, e.g. time limits.

The embodiments described herein may also include disposable and replaceable components, or elements, to minimize cross-contamination and to facilitate preparation for procedures. In particular, components that are likely to come into contact with the patient's tissue and bodily fluids are preferably discarded after a single use on the patient to minimize cross-contamination. Thus, embodiments may employ one or more use indicators which indicate whether a component of the system has been previously used. If it is determined from a use indicator that a component has been previously used, the entire system may be prevented from further operation so that the component cannot be reused and must be replaced.

For example, in the embodiment of FIG. 1, a use indicator 50 is employed to record usage data which may be read to determine whether the applicator 10 has already been used. In particular, the use indicator 50 may be a radio frequency identification (RFID) device, or similar data storage device, which contains usage data. The controller 40 may read and write usage data to the RFID 50. For example, if the applicator 10 has not yet been used, an indicator field in the RFID device 50 may contain a null value. Before the controller 40 delivers energy from the energy source 20 to the energy conducting element 11, it reads the field in the RFID device 50. If the field contains a null value, this indicates to the controller 40 that the applicator 10 has not been used previously and that further operation of the applicator 10 is permitted. At this point, the controller 40 writes a value to the field in the RFID device 50 to indicate that the applicator 10 has been used. When a controller 40 later reads the field in the RFID device 50, the non-null value indicates to the controller 40 that the applicator 10 has been used previously, and the controller will not permit further operation of the applicator 10. Of course, the usage data written to the RFID device 50 may contain any characters or values, or combination thereof, to indicate whether the component has been previously used.

In another example, where the applicator 410 and the vacuum ring 417 in the embodiment of FIG. 7A are separate components, use indicators 450A and 450B may be employed respectively to indicate whether the application 410 or the vacuum ring 417 has been used previously. Similar to the use indicator 50 described previously, the use indicators 450A and 450B may be RFID devices which the controller 440 may access remotely to read or write usage data. Before permitting operation of the applicator 410, the controller 40 reads the use indicators 450A and 450B. If the controller 440 determines from the use indicators 450A and 450B that the applicator 410 and/or the vacuum ring 417 has already been used, the controller 440 does not proceed and does not permit further operation of the applicator 410. When the applicator 410 and the vacuum ring 417 are used, the controller 440 writes usage data to both use indicators 450A and 450B indicating that the two components have been used.

In operation, a physician or other operator manually accesses a device, such as a computer keyboard, that interfaces with a controller, such as the controllers 40, 149, 240, and 340. The interface enables the operator to set up and/or initiate treatment. The system may request input, such as a predetermined amount of diopter correction that is required for a particular patient, baseline measurements of physical variables, astigmatism measurements, parameters for energy conduction to the cornea, timing and sequence information for the application of heat energy and pulses of coolant, and/or target values for physical variables that will be modified by treatment. The controller accepts program instructions that may access user input data or program selections from the interface and causes the system to implement a selected vision correction treatment.

In general, the controller may be a programmable processing device that executes software, or stored instructions, and that may be operably connected to the devices described above. In general, physical processors and/or machines employed by embodiments of the present invention for any processing or evaluation may include one or more networked or non-networked general purpose computer systems, microprocessors, field programmable gate arrays (FPGA's), digital signal processors (DSP's), micro-controllers, and the like, programmed according to the teachings of the exemplary embodiments of the present invention, as is appreciated by those skilled in the computer and software arts. The physical processors and/or machines may be externally networked with the image capture device, or may be integrated to reside within the image capture device. Appropriate software can be readily prepared by programmers of ordinary skill based on the teachings of the exemplary embodiments, as is appreciated by those skilled in the software art. In addition, the devices and subsystems of the exemplary embodiments can be implemented by the preparation of application-specific integrated circuits or by interconnecting an appropriate network of conventional component circuits, as is appreciated by those skilled in the electrical art(s). Thus, the exemplary embodiments are not limited to any specific combination of hardware circuitry and/or software.

Stored on any one or on a combination of computer readable media, the exemplary embodiments of the present invention may include software for controlling the devices and subsystems of the exemplary embodiments, for driving the devices and subsystems of the exemplary embodiments, for enabling the devices and subsystems of the exemplary embodiments to interact with a human user, and the like. Such software can include, but is not limited to, device drivers, firmware, operating systems, development tools, applications software, and the like. Such computer readable media further can include the computer program product of an embodiment of the present inventions for performing all or a portion (if processing is distributed) of the processing performed in implementing the inventions. Computer code devices of the exemplary embodiments of the present inventions can include any suitable interpretable or executable code mechanism, including but not limited to scripts, interpretable programs, dynamic link libraries (DLLs), Java classes and applets, complete executable programs, and the like. Moreover, parts of the processing of the exemplary embodiments of the present inventions can be distributed for better performance, reliability, cost, and the like.

Common forms of computer-readable media may include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

While various embodiments in accordance with the present invention have been shown and described, it is understood that the invention is not limited thereto. The present invention may be changed, modified and further applied by those skilled in the art. Therefore, this invention is not limited to the detail shown and described previously, but also includes all such changes and modifications.

What is claimed is:

1. A system for applying therapy to an eye, the system comprising:
   an electrical energy source;
   an electrical energy conducting element, comprising two conductors separated by a gap of a selected distance and extending from a proximal end to a distal end, the electrical conducting element operably connected to the electrical energy source and adapted to receive, at the proximal end, electrical energy generated by the electrical energy source and direct the electrical energy at the distal end, the distal end being positionable at an eye;
   a coolant supply; and
   at least one coolant delivery element in communication with the coolant supply, the at least one coolant delivery element being operable to deliver a pulse of coolant to the distal end, wherein the at least one coolant delivery element is positioned to deliver the pulse of coolant in the gap between the two conductors, wherein the electrical energy conducting element and the at least one coolant delivery element are included in a enclosed assembly, a dielectric material forming a bottom surface at the distal end, and the at least one coolant delivery element applies the pulse of coolant to the dielectric material positioned over the eye at the distal end, the at least one coolant delivery element delivering the coolant without forming a cooling layer between the dielectric and the eye.

2. The system according to claim 1, wherein the pulse of coolant is less than 100 milliseconds.

3. The system according to claim 1, wherein the pulse of coolant comprises a liquid with a boiling point below 37° C.

4. The system according to claim 1, wherein the electrical energy at the distal end has a frequency in the range from 500 MHz to 3000 Mhz.

5. The system according to claim 1, wherein the electrical energy directed at the distal end is delivered in an energy pulse.

6. The system according to claim 5, wherein the energy pulse is shorter than a thermal diffusion time in the eye.

7. The system according to claim 5, wherein the energy pulse is between 10 milliseconds and 1 second.

8. The system according to claim 7, wherein the energy pulse has a power in the range of 500 W to 3 KW.

9. The system according to claim 1, wherein the at least one coolant delivery element comprises a nozzle and an electrically controlled solenoid valve.

10. The system according to claim 1, further comprising a pressure relief structure in communication with an exterior environment, the pressure relief structure providing a passage of evaporated coolant to the exterior environment.

11. The system according to claim 10, wherein the pressure relief structure is a vent passage or a pressure relief valve.

12. The system according to claim 1, further comprising a vacuum source and at least one vacuum channel connected to the vacuum source, the at least one vacuum channel having an opening positioned at the distal end.

13. The system according to claim 12, wherein the vacuum channel opening is adapted to engage the eye and position the distal end for delivery of the pulse of coolant and the electrical energy to the eye.

14. The system according to claim 12, wherein the vacuum channel opening is adapted to draw away the coolant delivered by the pulse of the at least one nozzle.

15. The system according to claim 1, further comprising at least one heat sink element adapted to draw heat further from the distal end.

16. The system according to claim 1, further comprising a pressure relief structure in communication with an exterior environment, the pressure relief structure providing a release of pressure to the exterior environment.

17. The system according to claim 16, wherein the pressure relief structure is a pressure relief valve in communication with an exterior environment, the pressure relief valve adapted to open in response to pressure from the pulse of coolant delivered from the at least one nozzle.

18. The system according to claim 16, wherein the pressure relief structure is a vent passage in communication with an exterior environment, the vent passage providing a release of pressure to the exterior environment.

19. The system according to claim 1, wherein the electrical energy conducting element comprises a cylindrical outer conductor and a cylindrical inner conductor positioned within the outer conductor, the outer conductor and the inner conductor defining a annular gap extending from the proximal end to the distal end.

20. The system according to claim 19, wherein the at least one coolant delivery element includes more than one coolant delivery element positioned within the annular gap.

21. The system according to claim 1, further comprising a controller connected to the at least one coolant delivery element, the controller being operable to signal the at least one coolant delivery element to deliver the pulse of coolant toward the distal end, whereby the pulse of coolant is applied toward the eye positioned at the distal end.

22. The system according to claim 1, further comprising a controller connected to the electrical energy conducting element, the controller being operable to deliver the electrical energy from the electrical energy source to the conductors to deliver the electrical energy to the distal end.

23. The system according to claim 1, further comprising a controller connected to the at least one coolant delivery element and the electrical energy conducting element, the controller being operable, in a timed sequence, to signal the at least one coolant delivery element to deliver the pulse of coolant toward the distal end and to deliver the electrical energy from the electrical energy source to the conductors to deliver the electrical energy to the distal end.

24. The system according to claim 23, wherein the controller is operable to deliver the pulse of coolant to the distal end before and after delivering an energy pulse of electrical energy to the distal end.

25. A system for applying therapy to an eye, the system comprising:
an energy source;
a conducting element operably connected to the energy source and extending from a proximal end to a distal end, the conducting element adapted to direct energy from the energy source to the distal end, the distal end being positionable at an eye;
at least one coolant delivery element being operable to deliver a pulse of coolant to the distal end positioned over the eye; and
a low pressure source that generates a low pressure at the distal end and causes evaporative cooling at the distal end when the pulse of coolant is delivered to the distal end
wherein a dielectric material forms a bottom surface at the distal end of the conducting element, and the at least one coolant delivery element applies the pulse of coolant within a enclosed assembly to the dielectric material positioned over the eye at the distal end.

26. The system according to claim 25, wherein the low pressure source comprises a vacuum source coupled to at least one vacuum channel, the at least one vacuum channel having an opening positioned at the distal end and the vacuum source being operable to lower the pressure at the distal end.

27. The system according to claim 25, wherein the low pressure source comprises a vacuum source coupled to the enclosed assembly, the vacuum source being operable to lower the pressure within the enclosed assembly.

28. The system according to claim 25, further comprising a controller connected to the at least one coolant delivery element, the controller being operable to signal the at least one coolant delivery element to deliver the pulse of coolant to the distal end.

29. The system according to claim 25, further comprising a controller connected to the conducting element, the controller being operable to deliver energy from the energy source through the conducting element to the distal end.

30. The system according to claim 25, further comprising a controller connected to the at least one coolant delivery element and the conducting element, the controller being operable, in a timed sequence, to signal the at least one coolant delivery element to deliver the pulse of coolant to the distal end and to deliver energy from the energy source through the conducting element the conducting element to the distal end.

31. The system according to claim 30, wherein the controller is operable to deliver the pulse of coolant to the distal end before and after delivering an energy pulse to the distal end.

32. The system according to claim 25, wherein the energy source is an electrical energy source and the conducting element comprises two electrical conductors separated by a gap.

33. The system according to claim 25, wherein the pulse of coolant is less than 100 milliseconds.

34. The system according to claim 25, wherein the energy directed at the distal end is delivered in a energy pulse.

35. The system according to claim 25, further comprising a source of liquid with a boiling point below 37° C., wherein the at least one coolant delivery element delivers the pulse from the source of liquid.

36. The system according to claim 25, wherein the delivered pulse of coolant is drawn away from the distal end in association with the cooling at the distal end.

37. The system according to claim 25, wherein the electrical energy conducting element comprises a cylindrical outer conductor and a cylindrical inner conductor positioned within the outer conductor, the outer conductor and the inner conductor defining a annular gap extending from the proximal end to the distal end.

38. The system according to claim 37, wherein the at least one coolant delivery element applies the pulse of coolant within the annular gap.

39. The system according to claim 19, wherein the at least one coolant delivery element applies the pulse of coolant within the annular gap.

* * * * *